US012611288B2

(12) United States Patent
Gilgenbach Blume et al.

(10) Patent No.: US 12,611,288 B2
(45) Date of Patent: Apr. 28, 2026

(54) DENTAL IMPLANT, COMPONENT FOR DENTAL APPLICATIONS, IMPLANT SYSTEM FOR DENTAL APPLICATIONS, METHOD FOR FORMING A PROTECTIVE LAYER ON THE SURFACE OF AN IMPLANTABLE OR IMPLANT COMPONENT, IMPLANTABLE OR IMPLANT COMPONENT HAVING A PROTECTIVE LAYER, AND USE OF A PROTECTIVE LAYER

(71) Applicant: Nobel Biocare Services AG, Kloten (CH)

(72) Inventors: Jessica Gilgenbach Blume, Erlenbach (CH); Sebastian Bauer, Uster (CH); Angelines Gasser, Gattikon (CH); Tojo Razafiarison, Zurich (CH); Giulio Parcianello, Zurich (CH); Serif Ameti, Ossingen (CH); Michael Sandholzer, Rankweil (AT); Magdalena Pawelkiewicz Koebel, Bruttisellen (CH); Fabio Evangelisti, Zurich (CH); Philipp Lienemann, Zurich (CH); Vincent Milleret, Zurich (CH)

(73) Assignee: Nobel Biocare Services AG, Kloten (CH)

( * ) Notice: Subject to any disclaimer, the term of this patent is extended or adjusted under 35 U.S.C. 154(b) by 143 days.

(21) Appl. No.: 17/647,127

(22) Filed: Jan. 5, 2022

(65) Prior Publication Data

US 2022/0192794 A1 Jun. 23, 2022

Related U.S. Application Data

(63) Continuation of application No. 17/292,654, filed as application No. PCT/EP2019/080889 on Nov. 11, 2019, now Pat. No. 12,121,414.

(30) Foreign Application Priority Data

Nov. 12, 2018 (CH) ..................................... 01393/18

(51) Int. Cl.
A61C 8/00 (2006.01)
A61K 6/20 (2020.01)

(52) U.S. Cl.
CPC .......... *A61C 8/0015* (2013.01); *A61C 8/0045* (2013.01); *A61K 6/20* (2020.01); *A61C 2201/002* (2013.01)

(58) Field of Classification Search
CPC ................ A61C 8/0015; A61C 8/0045; A61C 2201/002; A61C 8/0013; A61K 6/20
See application file for complete search history.

(56) References Cited

U.S. PATENT DOCUMENTS 4,195,409 A 4/1980 Child
4,261,063 A 4/1981 Blanquaert
(Continued)

FOREIGN PATENT DOCUMENTS

CA 2 442 582 10/2002
CN 1392799 A 1/2003
(Continued)

OTHER PUBLICATIONS

Chandur P.K. Wadhwani, Richard O'Brien, Mathew T. Kattadiyil, Kwok-Hung Chung, "Laboratory technique for coloring titanium abutments to improve esthetics". The Journal of Prosthetic Dentistry, vol. 115, Issue 4, Mar. 24, 2016.*

(Continued)

*Primary Examiner* — Nicholas D Lucchesi
(74) *Attorney, Agent, or Firm* — Knobbe, Martens, Olson & Bear, LLP

(57) ABSTRACT
The present disclosure provides a dental implant configured to be inserted into a hole in jaw bone and to be at least (Continued)

partially situated in bone tissue when implanted. The dental implant includes a coronal implant region, the surface of which is at least partly covered by an oxide layer with an average thickness in the range from 60 nm to 170 nm and has an average arithmetical mean height Sa in the range from 0.1 μm to 1.0 μm.

16 Claims, 4 Drawing Sheets

(56) References Cited

U.S. PATENT DOCUMENTS

| | | | |
|---|---|---|---|
| 4,262,063 A | 4/1981 | Kudo et al. | |
| 4,330,891 A | 5/1982 | Branemark et al. | |
| 5,108,399 A | 4/1992 | Eitenmuller | |
| 5,152,794 A | 10/1992 | Davidson | |
| 5,180,394 A | 1/1993 | Davidson | |
| 5,282,861 A | 2/1994 | Kaplan | |
| 5,350,302 A | 9/1994 | Marlin | |
| 5,354,390 A | 10/1994 | Haszmann | |
| 5,489,306 A | 2/1996 | Gorski | |
| 5,697,779 A | 12/1997 | Sachdeva et al. | |
| 5,866,271 A * | 2/1999 | Stueber | C23C 28/00 |
| | | | 428/668 |
| 6,103,363 A | 8/2000 | Boire et al. | |
| 6,174,167 B1 | 1/2001 | Wohrle | |
| 6,183,255 B1 | 2/2001 | Oshida | |
| 6,220,861 B1 | 4/2001 | Kwon et al. | |
| 6,521,246 B2 | 2/2003 | Sapieszko et al. | |
| 6,527,554 B2 | 3/2003 | Hurson et al. | |
| 6,702,855 B1 | 3/2004 | Steinemann et al. | |
| 6,951,463 B2 | 10/2005 | Masuhara et al. | |
| 7,048,541 B2 | 5/2006 | Hall et al. | |
| 7,291,178 B2 | 11/2007 | Sul | |
| 7,410,502 B2 | 8/2008 | Ellingsen et al. | |
| 7,445,640 B2 | 11/2008 | Despres, III et al. | |
| 7,708,558 B1 | 5/2010 | Hall | |
| 7,771,774 B2 | 8/2010 | Berckmans, III et al. | |
| 7,951,285 B2 | 5/2011 | Zipprish | |
| 7,972,648 B2 | 7/2011 | Berckmans, III et al. | |
| 7,998,568 B2 | 8/2011 | Raja et al. | |
| 8,029,283 B2 | 10/2011 | Schwarz et al. | |
| 8,043,090 B1 | 10/2011 | Lyren | |
| 8,057,843 B2 | 11/2011 | Schlottig et al. | |
| 8,110,242 B2 * | 2/2012 | Hawkins | A61L 27/52 |
| | | | 623/23.76 |
| 8,241,036 B2 | 8/2012 | Breitenstein et al. | |
| 8,297,974 B1 | 10/2012 | Lyren | |
| 8,377,106 B2 | 2/2013 | Branemark et al. | |
| 8,399,008 B2 | 3/2013 | Webster et al. | |
| 8,408,906 B2 | 4/2013 | de Wild et al. | |
| 8,414,908 B2 | 4/2013 | Jin et al. | |
| 8,684,734 B1 | 4/2014 | Lyren | |
| 8,764,444 B2 | 7/2014 | Hansson | |
| 8,789,693 B2 | 7/2014 | Schlottig et al. | |
| 8,821,586 B2 | 9/2014 | Bjursten et al. | |
| 8,876,910 B2 | 11/2014 | Gilbert et al. | |
| 8,920,866 B2 | 12/2014 | Schlottig et al. | |
| 9,034,201 B2 | 5/2015 | Mayfield et al. | |
| 9,131,995 B2 | 9/2015 | Mayfield et al. | |
| 9,168,110 B2 | 10/2015 | Towse et al. | |
| 9,242,029 B2 | 1/2016 | Jennissen et al. | |
| 9,283,056 B2 | 3/2016 | Mayfield et al. | |
| 9,327,056 B2 | 5/2016 | Bandyopadhyay et al. | |
| 9,539,067 B2 | 1/2017 | Berckmans, III et al. | |
| 9,642,680 B2 | 5/2017 | Berner | |
| 9,642,708 B2 | 5/2017 | Fredriksson et al. | |
| 9,668,889 B2 | 6/2017 | Holt et al. | |
| 9,724,450 B2 | 8/2017 | Opie et al. | |
| 9,757,210 B2 | 9/2017 | Axen et al. | |
| 9,757,212 B2 | 9/2017 | Mayfield et al. | |
| 9,763,751 B2 | 9/2017 | Berckmans, III et al. | |
| 9,795,712 B2 | 10/2017 | Opie et al. | |
| 9,931,184 B2 | 4/2018 | Hall | |
| 9,968,715 B2 * | 5/2018 | Keil | A61L 31/088 |
| 9,993,319 B2 | 6/2018 | Berner et al. | |
| 10,040,727 B2 * | 8/2018 | Berner | C04B 41/009 |
| 11,357,600 B2 | 6/2022 | Memmolo et al. | |
| 11,918,434 B2 | 3/2024 | Memmolo et al. | |
| 12,121,414 B2 | 10/2024 | Gilgenbach Blume et al. | |
| 2001/0002994 A1 | 6/2001 | Masuhara et al. | |
| 2003/0158554 A1 | 8/2003 | Hall | |
| 2004/0121286 A1 | 6/2004 | Aravena et al. | |
| 2004/0236338 A1 | 11/2004 | Hall | |
| 2004/0267376 A1 * | 12/2004 | Suzuki | A61L 27/30 |
| | | | 623/23.5 |
| 2005/0019365 A1 | 1/2005 | Frauchiger et al. | |
| 2005/0103639 A1 | 5/2005 | Lu et al. | |
| 2005/0113834 A1 | 5/2005 | Breitenstein et al. | |
| 2005/0175658 A1 | 8/2005 | DiMauro et al. | |
| 2006/0149391 A1 | 7/2006 | Opie et al. | |
| 2006/0229715 A1 | 10/2006 | Istephanous et al. | |
| 2007/0202466 A1 | 8/2007 | Schwarz et al. | |
| 2007/0275350 A1 | 11/2007 | Hall | |
| 2008/0004691 A1 | 1/2008 | Weber et al. | |
| 2008/0097618 A1 | 4/2008 | Baker et al. | |
| 2008/0213726 A1 * | 9/2008 | Schlottig | A61L 27/10 |
| | | | 433/201.1 |
| 2008/0220394 A1 | 9/2008 | Berckmans et al. | |
| 2008/0269910 A1 | 10/2008 | Ellingsen et al. | |
| 2009/0011384 A1 | 1/2009 | Collins | |
| 2009/0132048 A1 | 5/2009 | Denzer | |
| 2009/0220913 A1 | 9/2009 | Geis-Gerstorfer | |
| 2010/0112519 A1 | 5/2010 | Hall et al. | |
| 2010/0168854 A1 | 7/2010 | Luers et al. | |
| 2011/0233169 A1 | 9/2011 | Mayfield et al. | |
| 2011/0311946 A1 | 12/2011 | Sailer et al. | |
| 2012/0021008 A1 * | 1/2012 | De Bruijn | A61P 19/08 |
| | | | 424/602 |
| 2012/0024710 A1 * | 2/2012 | Turner | C25D 11/26 |
| | | | 205/199 |
| 2012/0040102 A1 | 2/2012 | Meredith | |
| 2012/0189833 A1 * | 7/2012 | Suchanek | C04B 35/80 |
| | | | 501/153 |
| 2012/0288699 A1 | 11/2012 | Ahlberg et al. | |
| 2013/0045360 A1 | 2/2013 | Ibacache et al. | |
| 2013/0233717 A1 | 9/2013 | Disegi | |
| 2014/0011161 A1 | 1/2014 | Berckmans, III et al. | |
| 2014/0141201 A1 * | 5/2014 | Berner | C04B 41/85 |
| | | | 427/372.2 |
| 2014/0170600 A1 | 6/2014 | Koncewicz | |
| 2014/0174939 A1 | 6/2014 | Hall | |
| 2014/0178639 A1 | 6/2014 | Berner | |
| 2014/0329052 A1 | 11/2014 | Gittens Ibacache et al. | |
| 2014/0342314 A1 | 11/2014 | Chamblee | |
| 2014/0342316 A1 | 11/2014 | Berner et al. | |
| 2014/0343687 A1 | 11/2014 | Jennissen | |
| 2015/0037758 A1 | 2/2015 | Tatum, Jr. et al. | |
| 2015/0056573 A1 | 2/2015 | Collins et al. | |
| 2015/0086943 A1 | 3/2015 | Schwarz et al. | |
| 2015/0209480 A1 | 7/2015 | Byon et al. | |
| 2015/0245899 A1 | 9/2015 | Lyngstadaas et al. | |
| 2015/0289951 A1 | 10/2015 | Mayfield et al. | |
| 2015/0351874 A1 | 12/2015 | Axén et al. | |
| 2016/0030140 A1 | 2/2016 | Towse et al. | |
| 2016/0045289 A1 | 2/2016 | Berckmans, III et al. | |
| 2016/0058920 A1 | 3/2016 | Ha et al. | |
| 2016/0120625 A1 | 5/2016 | Berner | |
| 2016/0120626 A1 | 5/2016 | Berner | |
| 2016/0136336 A1 | 5/2016 | Jennissen et al. | |
| 2016/0228992 A1 | 8/2016 | Bandyopadhyay et al. | |
| 2016/0278885 A1 | 9/2016 | Kirsten et al. | |
| 2017/0001920 A1 * | 1/2017 | Berner | C04B 41/5042 |
| 2017/0079752 A1 | 3/2017 | Hall | |
| 2017/0112962 A1 | 4/2017 | Storey et al. | |
| 2017/0196662 A1 | 7/2017 | Perler et al. | |
| 2017/0218522 A1 | 8/2017 | Baytekin-Gerngross et al. | |
| 2017/0224458 A1 | 8/2017 | Martin et al. | |
| 2017/0258556 A1 | 9/2017 | Watanabe et al. | |
| 2018/0153660 A1 | 6/2018 | Berner | |
| 2018/0353268 A1 | 12/2018 | Memmolo et al. | |
| 2019/0046299 A1 | 2/2019 | Kim | |
| 2019/0117344 A1 | 4/2019 | Schwarz et al. | |

(56)                References Cited

U.S. PATENT DOCUMENTS

| 2022/0087784 A1 | 3/2022 | Gilgenbach Blume et al. |
| 2022/0378554 A1 | 12/2022 | Memmolo et al. |
| 2023/0070222 A1 | 3/2023 | Nagel et al. |
| 2025/0134632 A1 | 5/2025 | Gilgenbach Blume et al. |

FOREIGN PATENT DOCUMENTS

| CN | 1817319 A | 8/2006 |
| CN | 103736148 A | 4/2014 |
| CN | 106725928 | 5/2017 |
| DE | 3445848 A1 | 6/1986 |
| DE | 4311772 A1 | 10/1993 |
| DE | 4216122 A1 | 11/1993 |
| DE | 10 2006 021968 A1 | 11/2007 |
| EP | 0 388 576 A1 | 9/1990 |
| EP | 0 676 179 A2 | 10/1995 |
| EP | 0 806 211 A1 | 11/1997 |
| EP | 1 191 901 B1 | 4/2005 |
| EP | 1 527 790 A1 | 5/2005 |
| EP | 1 652 963 A1 | 5/2006 |
| EP | 1 825 830 A1 | 8/2007 |
| EP | 1 847 278 A1 | 10/2007 |
| EP | 1 492 579 B1 | 9/2008 |
| EP | 1 196 110 B1 | 1/2009 |
| EP | 1 534 168 B1 | 6/2010 |
| EP | 1 980 276 B1 | 3/2011 |
| EP | 2 292 178 A1 | 3/2011 |
| EP | 1 397 168 B1 | 5/2011 |
| EP | 1 825 829 B1 | 8/2011 |
| EP | 2 161 000 B1 | 8/2011 |
| EP | 1 534 175 B1 | 10/2011 |
| EP | 2 160 998 B1 | 4/2012 |
| EP | 2 436 336 A1 | 4/2012 |
| EP | 2 319 461 B1 | 9/2012 |
| EP | 2 289 460 B1 | 4/2013 |
| EP | 2 398 518 B1 | 4/2013 |
| EP | 1 274 470 B1 | 6/2013 |
| EP | 1 696 816 B2 | 10/2013 |
| EP | 2 537 485 B1 | 5/2015 |
| EP | 1 982 671 B1 | 3/2016 |
| EP | 3 011 980 A1 | 4/2016 |
| EP | 1 622 656 B1 | 7/2016 |
| EP | 3 195 825 A1 | 7/2017 |
| EP | 3 854 342 A1 | 7/2021 |
| GB | 2560484 | 9/2018 |
| JP | H03-47264 | 2/1991 |
| JP | 07-328037 A | 12/1995 |
| JP | 11-033106 | 2/1999 |
| JP | 2000-116673 | 4/2000 |
| JP | 2002-102330 | 4/2002 |
| JP | 2005-509494 | 4/2005 |
| JP | 2007-252897 | 10/2007 |
| JP | 2007-527758 | 10/2007 |
| JP | 2010-533012 | 10/2010 |
| JP | 5037136 B2 | 9/2012 |
| JP | 2013-022036 | 2/2013 |
| JP | 5523709 B2 | 6/2014 |
| JP | 2014-204867 | 10/2014 |
| JP | 2018-504152 | 2/2018 |
| SE | 514202 | 1/2001 |
| SE | 516282 | 12/2001 |
| WO | WO 00/072776 A1 | 12/2000 |
| WO | WO 00/072777 A1 | 12/2000 |
| WO | WO 01/076653 A1 | 10/2001 |
| WO | WO 02/078759 A1 | 10/2002 |
| WO | WO 02/096475 A1 | 12/2002 |
| WO | WO 03/003937 A1 | 1/2003 |
| WO | WO 03/063925 A1 | 8/2003 |
| WO | WO 03/086495 A1 | 10/2003 |
| WO | WO 2004/008984 A1 | 1/2004 |
| WO | WO 2004/091424 A1 | 10/2004 |
| WO | WO 2005/055858 A1 | 6/2005 |
| WO | WO 2005/055859 A1 | 6/2005 |
| WO | WO 2005/055860 A1 | 6/2005 |
| WO | WO 2006/004686 A2 | 1/2006 |
| WO | WO 2007/059038 A2 | 5/2007 |
| WO | WO 2007/091155 A1 | 8/2007 |
| WO | WO 2007/118734 A1 | 10/2007 |
| WO | WO 2010/094968 A2 | 8/2010 |
| WO | WO 2011/066098 A1 | 6/2011 |
| WO | WO 2013/056844 A1 | 4/2013 |
| WO | WO 2014/195025 A2 | 12/2014 |
| WO | WO 2014/195027 A2 | 12/2014 |
| WO | WO 2015/044401 A2 | 4/2015 |
| WO | WO 2015/132325 A1 | 9/2015 |
| WO | WO 2015/145450 A1 | 10/2015 |
| WO | WO 2016/009372 A1 | 1/2016 |
| WO | WO 2016/042515 A1 | 3/2016 |
| WO | WO 2016/062882 A1 | 4/2016 |
| WO | WO 2016/096734 A1 | 6/2016 |
| WO | WO 2016/118038 A1 | 7/2016 |
| WO | WO 2016/185186 A1 | 11/2016 |
| WO | WO 2016/189099 A1 | 12/2016 |
| WO | WO 2017/009500 A1 | 1/2017 |
| WO | WO 2017/075364 A1 | 5/2017 |
| WO | WO 2017/210758 A1 | 12/2017 |
| WO | WO 2018/011604 A2 | 1/2018 |

OTHER PUBLICATIONS

International Search Report mailed May 19, 2020 in Application No. PCT/EP2019/080889 in 6 pages.
Tiunite, Website nobelbiocare.com, dated Jul. 20, 2011 in 1 page.
Medienmitteilung—Nobel Bioacare unterzeichnet mit Wyeth eine exklusive Lizenzvereinbarung fur die Nutzung des rhBMP-2-Proteins fur Dentalimplantate, dated Jun. 9, 2005, 2 pages.
TiUnite—Die einzgartige Titanoxidoberfläche, jetz neu im Branemark-System, Nobel Biocare Catalog, cited on Aug. 9, 2011 in an Opposition against European Patent EP 1696816 (European Application No. EP 04820332.7), 8 pages.
Branemark System, STERI-OSS, Replace, PROCERA, GORE—Nobel Biocare Catalog, dated Aug. 9, 2011, 10 pages.
All in One—Nobel Biocare Catalog, dated 2001, 10 pages.
Replace—TiUnite—Nobel Biocare Catalog, dated 2001, 6 pages.
Replace Introduces TiUnite, A Unique Oxidized Titanium Surface—Nobel Biocare Catalog, dated 2001, 10 pages.
Battiston, G.A. et al. "Dental Implants of Complex Form Coated by Nanostructured TiO2 Thin Films via MOCVD," Materials Science Forum, vol. 352, pp. 151-158, dated 2000.
Bjursten et al., "Titanium dioxide nanotubes enhance bone bonding in vivo," J. of Biomedical Materials Research Part A, Wiley InterScience, pp. 1218-1224, dated Apr. 2, 2009.
Born, R. et al. "Surface analysis of titanium based biomaterials," J. Anal. Chem., 361: 697-700, 1998.
Chen Z. X. et al., "Surface characteristics and in vitro biocompatibility of titanium anodized in a phosphoric acid solution at different voltages," Biomedical Materials, Institute of Physics Publishing, Bristol, GB, vol. 4, No. 6, p. 65003, Dec. 1, 2009.
Del Curto, B. et al., "Decreased bacterial adhesion to surface-treated titanium," The International Journal of Artificial Organs, vol. 28, No. 7, pp. 718-730, dated 2005.
Expressing Universality, dated Sep. 8, 2012 in 8 pages.
Gao et al., "Micro/Nanostructural Porous Surface on Titanium and Bioactivity," J. of Biomedical Materials Research Part B: Applied Biomaterials, Wiley InterScience, pp. 335-341, dated Oct. 6, 2008.
Gong et al., "Titanium oxide nanotube arrays prepared by anodic oxidation," J. Mater. Res., vol. 16, No. 12, pp. 3331-3334, dated Dec. 2001.
Hall, J. et al., "Properties of a new porous oxide surface on titanium implants," Applied Osseointegration Research, vol. 1, pp. 5-8, dated 2000.
Hanaor et al. "Review of the anatase to rutile phase transformation," Journal of Material Science, vol. 46, pp. 855-874, dated 2011.
Ignatov, V. "Biocompartible Coatings on Titanium Implants," Science and Technology, pp. 197-201, Jun. 28, dated 2003.
Jaeggi C. et al., "Anodic thin films on titanium used as masks for surface micropatterning of biomedical devices," Surface and Coatings Technology, Elsevier, Amsterdam, NL, vol. 200, No. 5-6, pp. 1913-1919, dated Nov. 21, 2005.

(56)          References Cited

OTHER PUBLICATIONS

Kim et al., "Electrochemical surface modification of titanium in dentistry," Dental Materials Journal 28(1), 20-36, dated 2009.

Kokubo, T et al. "Novel bioactive materials with different mechanical properties," vol. 24, No. 13; pp. 2-16, dated Jun. 2003.

Liu et al., "Surface modification of titanium, titanium alloys, and related materials for biomedical applications," Materials Science and Engineering R 47 pp. 49-121, dated 2004.

Lüers et al., "Protecting ultra- and hyperhydrophilic implant surfaces in dry state from loss of wettability", Current Directions in Biomedical Engineering 2016; vol. 2, No. 1, pp. 557-560, Sep. 30, 2016.

Miyazaki, T. et al., "Auger Electron Spectroscopic Studies of Titanium Implants Treated by Several Finishing Porcedures," J. Showa Univ. Dent. Soc. 11:322-326, dated 1991.

Parkhutik et al., "Theoretical modelling of porous oxide growth on aluminium," J. Phys. D: Appl. Phys. 25, pp. 1258-1263, dated 1992.

Rossi, S. et al., "Comparison between sol-gel-derived anatase- and rutile-structured TiO2 coatings in soft-tissue environment," J. Biomedical Materials Research Part A, pp. 965-974, Mar. 2, 2007.

Ruano, R. et al., "Effect of a Ceramic and a Non-Ceramic Hydroxyapatite on Cell Growth and Procollagen Synthesis of Cultured Human Gingival Fibroblasts," J. Periodontol., vol. 71, No. 4, pp. 540-545, dated Apr. 2000.

Rupp et al., "Enhancing surface free energy and hydrophilicity through chemical modification of microstructured titanium implant surfaces," J. Biomed Mater Res A. dated 2006, vol. 76, pp. 323-334.

Schroeder, A. et al. "Orale Implantologic," Georg Thieme Verlag Stuttgart dated 1994, in 5 pages.

Smith, G.C. et al., "Soft tissue response to titanium dioxide nanotube modified implants," Acta Biomaterialia 7, 3209-3215, dated 2011.

Sul, Young-Taeg, "The significance of the surface properties of oxidized titanium to the bone response: special emphasis on potential biochemical bonding of oxidized titanium implant," Biomaterials 24, pp. 3893-3907, dated 2003.

Sul, YT et al., "Resonance frequency and removal torque analysis of implants with turned and anodized surface oxides," Clinical Oral Implants Research, 13, pp. 252-259, dated 2002.

Wennerberg et al., "Current knowledge about the hydrophilic and nanostructured SLActive surface," Clinical, Cosmetic and Investigational Dentistry, Dovepress, pp. 59-67, dated Sept. 5, 2011.

Wennerberg et al., "On Implant Surfaces: A Review of Current Knowledge and Opinions," International J. of Oral & Maxillofacial Implants, vol. 25, No. 1, pp. 63-74, dated Jan.-Feb. 2010.

Zhao et al., "The influence of hierarchical hybrid micro/nano-textured titanium surface with titania nanotubes on osteoblast functions," Biomaterials 31, pp. 5072-5082, dated Apr. 2, 2010.

Zhao, Jingmei, "Oral titanium implant surface modification and its biological properties", China Master's Theses Full-text Database, Engineering Technology, series I, B022-123, dated published on Jul. 15, 2013.

Examination Report dated Jun. 3, 2025 for Australian Application No. 2019379758; 4 pages.

Yamagami et al., "Ultra-structural evaluation of an anodic oxidated titanium dental implant", Dental Materials Journal 2014; 33(6), pp. 828-834; 7 pages.

* cited by examiner

DENTAL IMPLANT, COMPONENT FOR DENTAL APPLICATIONS, IMPLANT SYSTEM FOR DENTAL APPLICATIONS, METHOD FOR FORMING A PROTECTIVE LAYER ON THE SURFACE OF AN IMPLANTABLE OR IMPLANT COMPONENT, IMPLANTABLE OR IMPLANT COMPONENT HAVING A PROTECTIVE LAYER, AND USE OF A PROTECTIVE LAYER

CROSS-REFERENCE TO RELATED APPLICATIONS

This application is a continuation of U.S. patent application Ser. No. 17/292,654, filed on May 10, 2021, which is a national stage application under 35 U.S.C. § 371 of International Application No. PCT/EP2019/080889, filed on Nov. 11, 2019, which published in English as WO 2020/099334 A2 on May 22, 2020 and which claims priority benefit of CH Patent Application No. 01393/18 filed on Nov. 12, 2018.

BACKGROUND

Technical Field

The present invention relates to a dental implant, a component for dental applications, an implant system for dental applications, a method for forming a protective layer on the surface of an implantable or implant component, an implantable or implant component and a use of a protective layer.

Description of the Related Art

For decades dental implants have been successfully used to replace lost or missing teeth. One of the overriding challenges in implant dentistry is to modify the properties of soft tissue adhering surfaces to promote optimal soft-tissue adherence at the same time as minimizing bacterial adhesion and bio film formation and allowing the maintenance of good oral hygiene. In addition, another major objective is to bespokedly design those surfaces of a dental implant that come into contact with bone tissue. The aim here is to enable best possible osseointegration of the dental implant, which is the very foundation for the implant to function over many years and for the suppression of post-implantation complications. In addition to all the medical and biological requirements, esthetics also plays a role. Here the aim is to achieve an appearance that is as close as possible to a natural tooth and to avoid that any parts of the dental implant structure are visible.

Various implant structures and designs of fixtures, spacers and prosthetic components have been presented over the years in order to at least partially address the above needs. In addition, various substances and compositions have been proposed for being used as coatings on substrates, such as to form an implant surface. However, as will be recognized after having read the technical background of the present application, the human body is a highly advanced and complex environment and it is not an obvious task how to design an implant structure to overcome the described issues.

One way to treat dental implants that have been used for and shown excellent results for osseointegration in bone is the TiUnite® surface. Said surface has a titanium oxide layer with a homogeneously distributed pore structure with pore sizes typically in the range of 50 nm-5 micron and phosphorous is embedded within the titanium oxide. The surface roughness Sa is approximately 1.2 microns. The TiUnite® surface is explained in detail in Jan Hall and Jukka Lausmaa, "Properties of a new porous oxide surface on titanium implants", Applied Osseointegration Research, vol. 1, pp. 5-8, 2000.

An advanced dental implant surface design is described in WO 2016/096734 A1. Therein, a dental implant, preferably a screw-like dental implant exhibits a surface design that basically changes along the longitudinal axis of the dental implant depending on the in-situ environment each individual part of the dental implant encounters. Hence, the dental implant therein has a comparably smooth surface at the coronal end of the dental implant, which is easy to clean and promotes good soft tissue connection. Towards the apical end of the dental implant, surface roughness and porosity increase and are maximized to provide a surface for optimal in-growth of jaw bone tissue and osseointegration. Parts of the present invention and disclosure aim at modifying and further improving said dental implant design.

In addition to challenges that arise with respect to implantation, there are challenges before that. One such challenge is to standardize and control design properties of (dental) implants and abutments over the shelf life. Most commercial implants are stored in sterile packaging and have an expiration date 5 years after manufacturing.

During storage, atmospheric molecules, such as hydrocarbons can deposit on the implant, causing contamination. Increased deposition of hydrocarbons on titanium were shown to correlate with a decreased surface energy (hydrophilicity) and reduced protein and osteogenic cell adhesion.

In the event of critical amounts of hydrocarbons on the surface, the implant osseointegration as well as a decrease in the biomechanical strength of the bone-titanium integration were reported, when compared to freshly prepared titanium surface. To prevent from such potential effects during storage time on the biological performance of medical implants, packaging strategies for preserving the surface state have been developed, such as wet storage or dry storage using a soluble protective layer resulting in pristine surfaces after extended storage time.

Storing the implant in a wet packaging induces changes in the implant surface properties over time (due to e.g. oxidation, formation of nanostructures, etc.). The nanostructures moreover are affected by other environmental parameters like temperature and pressure, which cannot be always controlled throughout implant storage.

For these reasons, dry storage is preferred to wet storage. A strategy could be to store the samples in a controlled protective environment (i.e. inert gas). The difficulty is to ensure that the packaging remains gas impermeable throughout storage and that no easy control can be implemented at the clinician site to show that the packaging has not been compromised.

A last approach is to protect the surface in a dry state by applying a protective layer to the implants. The protective layer is typically applied by a dip and dry process. The protective layer prevents contaminants present in the air from reaching the surface. Upon contact with body fluid such as saliva or blood, the protective layer should be dissolved, ideally revealing the pristine surface with a preserved chemistry and surface energy.

Rupp et al describe a study on enhancing the surface free energy and hydrophilicity through chemical modification of microstructured titanium implant surfaces, published in J Biomed Mater Res A. 2006 February; 76(2):323-34. This article describes the wet storage of an implant in a sodium chloride solution.

An approach utilizing this finding is described in WO 2007/118734 A1. In this case, the dried salt layer forms a physical barrier that protects the implant surface during dry storage, and the salt stays on the implant surface at the time of implantation. For this reason, the salts are limited to those that are readily soluble in body fluids. All examples of WO 2007/118734 A1 use an aqueous 0.15M NaCl solution.

A study on the protective effect of salt layers formed from different salt solutions in different concentrations is described in an article by Lifers et al in Current Directions in Biomedical Engineering 2016; 2(1): 557-560. The solutions tested include those that contain only sodium phosphates, only potassium phosphates, only magnesium phosphates, or mixed solutions of sodium and potassium chlorides and phosphates. One of the solutions also contains calcium chloride and magnesium chloride.

The study examines the influence of salt layers formed from such solutions in different concentrations on a titanium implant on the dynamic contact angle of the implant. The worst results were obtained for a solution containing 136.8 mM NaCl, 2.7 mM KCl, 1.5 mM $KH_2PO_4$ and 8.1 mM $Na_2HPO_4$, for a solution containing only sodium phosphates at a total concentration of 96 mM, for a solution containing only potassium phosphates at a total concentration of 9.6 mM, and for a solution containing only ammonium phosphate at a concentration of 100 mM. All other solutions/concentrations were equally good, as no change in contact angle after storage is indicated for them. The pH of all solutions tested in this study that contained monovalent alkali metal cations was 7.3 or higher, while for earth alkaline metal divalent cation (Mg or Ca) containing solutions a pH of 6.7, 6.3, 3.5 and 2.7, respectively is reported. The solutions having a pH of 6.3 and 6.7 are reported to lead to an decrease in surface energy as expressed by the dynamic contact angle, and thus do not provide the desired protection to full extent. The solutions having a pH of 2.7 and 3.5, respectively, contain only divalent Mg cations. Mg and Ca (earth alkaline metal salts) salts are generally less soluble as compared to the corresponding salts of monovalent species (alkaline metal salts), and may thus be more difficult to dissolve. It is also reported that the solution containing only Mg salt led to a poor allocation of salt layer on the surface at low concentrations of 10 mM, and that syrup-like residues remain on the surface at higher concentrations.

The document further reports that the surface appearance differed between the salt layers, and that a homogeneous film could not be obtained in all instances. These problems were in particular encountered for sodium phosphate solutions.

The authors conclude that a potassium phosphate buffer solution having a pH of 7.6 provides the best system for conservation of titanium implant surfaces, as this provides the best results with regard to preservation of hydrophilicity of the salt layer surface and optical appearance.

There are concerns about possible negative impacts on biointegration that could occur in case of a salt layer that is optimized for preservation of hydrophilicity of the salt layer surface and optical appearance. Specifically, there is concern that such layers could remain to a larger extent on the implant surface, thereby possibly disturbing osseointegration. Also, in many cases the underlying surface of an implant is adapted to have a certain structure and surface composition, and these features may not be able to exhibit their biological function in case a salt layer remains, fully or in part, on the implant surface.

It would thus be preferred if the salt layer could be removed quickly and fully upon contact with liquids such as water, body fluid or saliva, thus as to minimize the risk of impairing the healing process due to remaining components of the protective layer on the implant. There is also a need for a salt layer that is able to reveal the pristine underlying surface of a dental implant quickly. The underlying surface of the dental implant should have high surface energy (hydrophilicity) after the salt layer is dissolved.

SUMMARY

The present invention seeks to provide a dental implant configured to be inserted into a hole in jaw bone that exhibits superior tissue integration properties, soft-tissue seal formation and at the same time a reduced risk of post-implantation complications, in particular arising from deleterious biofilm formation. The present invention further strives to provide a dental implant that facilitates easier and better cleaning of parts of the implant in particular those adjacent to tissue, exposed to the buccal cavity environment and prone to deleterious biofilm formation, thereby improving dental prophylaxis, oral hygiene and gingival health. A further objective of the present invention is to provide a dental implant with improved in-situ appearance and esthetics as compared to conventional implants.

The present invention further provides a dental component other than a dental implant, preferably a dental abutment that is able to support and improve soft tissue attachment, minimize bacteria accumulation and has better in-situ appearance and esthetics as compared to conventional components and abutments.

Furthermore, the present invention makes available an innovative implant system achieving overall superior properties by combining the dental implant and the component, preferably the dental abutment, of this invention.

Yet another aspect of this invention is providing a method for forming a protective layer on the surface of an implant or implant component such that changes in the physiochemical surface properties thereof during dry-storage are prevented and upon use, the protective layer can be easily and fully removed, revealing a surface that is pristine and basically possesses the same properties as that of a freshly manufactured implant or implantable component. A further and related objective of the present invention is to provide an implantable or implant component with a protective layer that basically preserves the pristine and functional as-manufactured surface. Using the protective layer for dry storage of an implantable or implant component is a final related aspect of this invention.

It is a further object of the present invention to provide a means for protecting the surface of an implantable and/or implant component against contamination and/or against loss of hydrophilicity, as e.g. caused by uptake of hydrophobic substances from the air, which means can be easily applied for providing protection, whereby the protected implant can be easily handled and stored, and which means can be easily and fully removed to thereby reveal the underlying surface of the implant, to minimize the risk of interference with the healing process.

The above problems are solved and objectives achieved by means of the invention as outlined below and as defined in the appended claims.

Further advantages and objects of the present invention will become more apparent in view of the following detailed description.

The terminology used in the following description is not intended to be limiting the invention.

All methods for determining parameters and properties described below may be used, in addition to methods used in the art or standardized. In case of discrepancies or incompatibilities, the present disclosure prevails.

Water contact angles can be determined according to DIN 55660-2. The contact angle quantifies the wettability of a surface and is representative of its free surface energy and hydrophilicity. The term "contact angle" refers to the contact angle of water on a surface. The measurement is carried out according to the sessile drop method using e.g. a device EasyDROP DSA20E, Krüss GmbH, using a drop size of 0.3 μl. Contact angles can be calculated by fitting a circular segment function to the contour of the droplet placed on the surface. The term "hydrophilic" may refer to contact angles of 30° or less.

In the present invention, all parameters and product properties relate to those measured under standard conditions (25° C., 101 kPa) unless stated otherwise or prescribed by a certain standard or test protocol.

The term "about" means that the amount or value in question may be the specific value designated or some other value in its neighborhood, generally within a range of ±5% of the indicated value. As such, for instance the phrase "about 100" denotes a range of 100±5. All values given below are deemed to be modified by the word "about", unless the context provides a different meaning or dictates otherwise.

The term and/or means that either all or only one of the elements indicated is present. For instance, "a and/or b" denotes "only a", or "only b", or "a and b together". In the case of "only a" the term also covers the possibility that b is absent, i.e. "only a, but not b".

The term "comprising" as used herein is intended to be non-exclusive and open-ended. A composition or article comprising certain components thus may comprise other components besides the ones listed. However, the term also includes the more restrictive meanings "consisting of" and "consisting essentially of", which are used synonymous with "made of" and "made essentially of", respectively.

Whenever a range is expressed as "from x to y", or the synonymous expression "x-y", the end points of the range (i.e. the value x and the value y) are included. The range is thus synonymous with the expression "x or higher, but y or lower".

The various embodiments disclosed herein can be combined in any manner, unless they are clearly not compatible. Also, any given range is deemed to include and disclose any value falling within that range.

Dental Implant

The dental implant according to the present invention and disclosure is configured to be inserted into a hole in jaw bone and to be at least partially situated in bone tissue when implanted, and comprises a coronal implant region, the surface of which is at least partly, preferably fully, covered by an oxide layer with an average thickness in the range from 60 nm to 170 nm and has an arithmetical mean height Sa in the range from 0.1 μm to 1.0 μm.

The expression "dental implant" is to be construed widely as an entity that is configured to be used in human or animal dentistry. Furthermore, the dental implant according to this invention is configured to be placed at least partially inside a hole formed in jaw bone in order to provide foundation for further implant constituents that are placed and/or fixed thereto. As a non-exclusive and non-limiting example, the dental implant of the present invention may be a threaded artificial dental root that can threadedly, i.e., via a thread, engage with the jaw bone and extends from the oral cavity through the gingiva and further into soft and hard bone tissue and can be referred to as "dental screw". For the sake of intelligibility and purely for illustrative purposes, the following explanations may occasionally mention a "dental screw" as a non-limiting example of the dental implant. Non-threaded implants, for instance, are within the scope of the invention. Also within the scope of the invention are multi-part dental implants that are assembled from and by several individual physical entities.

The expressions "coronal" as well as all other similar terminology found in this disclosure, for example, "apical" are to be construed in line with the usual meaning they possess in the context of dentistry. Hence, the coronal implant region is in-situ located adjacent where normally the crown region of a tooth at the site of implantation would be situated and an apical implant region would be spaced away from said coronal region in the direction towards the jaw bone and is located where the root region of a tooth at the site of implantation would normally be situated. Furthermore, the so described coronal and apical implant regions are to be construed as indicating a "start point" and an "end point" respectively for the evolution of the below further specified implant surface characteristics. More specifically, the apical end or apex of the dental implant and the coronal end of the dental implant are said points.

The dental implant has a surface that basically forms a transitional interface between the base material associated to the dental implant, for example, the implant base/bulk material or an implant coating and in the widest sense the oral environment. The oral environment can comprise particular tissues like gingival soft tissue or various types of bone tissue, but is not limited to a particular type. The interface can also be between the implant and the buccal cavity, i.e., so as to basically be an interface between the implant and any conceivable physiological substance encountered in the buccal cavity, for example, the saliva. Said environment encountered depends on the region/part of the implant (coronal, apical, intermediate/transition) and the way of implantation, for example, submerged, flush or protruded. The terminology "surface of the implant/component/abutment" or "surface of region X/Y/Z" preferably refers to outer and outermost surfaces, which as explained above, delimit the implant relative to the oral environment. In contrast thereto, inner surfaces of the dental implant or component/abutment, for example, openings/cavities/bores facing towards the inside are not normally exposed thereto. However, in some scenarios these inner surfaces may also benefit from the characteristics of the present invention, in particular, if any exposure to the oral environment is conceivable—intentionally or not, and are thus not excluded. In other words, the beneficial surface properties described herein can also be applied to inner surfaces of the dental implant or the component/dental abutment to be described later and are part of the present invention.

According to the present invention and disclosure, the dental implant has a coronal implant region, which is located in the uppermost part of the dental implant. In the present technical field said coronal implant region is also often referred to as "collar region", which can be seen as an equivalent term. The surface of the coronal implant region is at least partially, preferably fully covered by an oxide layer. This includes the options that either only one distinct region of the coronal implant region's surface or a plurality of surface regions have the oxide layer formed thereon or that even the entire coronal implant region is fully covered with said oxide layer. The latter may be preferred for functional reasons as will be outlined later. The general nature of the oxide layer is not particularly limited. The term "oxide layer" is to be understood as a layer that predominately comprise, is made of or fully consists of at least one oxide, i.e., a compound of oxygen and a least one other element. For the present invention, metal oxides (Me-O) and specifically titanium oxides, in particular $TiO_2$, are preferred compounds for the oxide layer. Conceivable are oxide layers that are formed by conversion of superficial implant material, for example, via phase transitions or surface reactions on the implant surface. Such layer types do normally not involve the application of additional material on the implant surface and originate instead inherently, from the implant base material itself being converted/transformed by means of any of the known procedures. However, it is conceivable e.g. in case of an electrolytic process for forming the oxide layer that elements from the electrolyte may be incorporated into the oxide layer. Such elements can for instance comprise phosphates and/or phosphorus. Other conceivable types of oxide layers comprise layers applied to the implant surface via coating processes, in which conventionally, additional material is applied to a largely unchanged/native implant surface or simply the implant base material.

The above oxide layer has a thickness in the range of 60 nm to 170 nm. The oxide layer thickness can be measured on images of axial cross sections of the dental implant as will be detailed further below. In addition, the surface of the coronal implant region has an arithmetical mean height Sa in the range from 0.1 μm to 1.0 μm. The parameter Sa is well-known to the skilled person and a standard parameter to characterize the areal roughness of a surface. A synonymous expression used for Sa is thus "surface roughness", which can also be used for the present invention. Parameter Sa can be determined from white light interferometry measurements as will be detailed further below. Preferably, the above Sa is an average area roughness, meaning that it was measured at various position of the coronal implant region or any implant region of relevance and then the mathematical average calculated from all of the measurements. It is further to be noted that the here described surface roughness Sa preferably reflects the surface of the coronal implant region including the oxide layered formed thereon. In other words, having the oxide layer formed on the surface of the dental implant's base material determines the overall surface roughness Sa of the surface. The measured surface roughness may be seen as a superposition of the surface roughness of the surface of the dental implant's base material, for example, as created by machining and the surface of the oxide layer on top of that. The original/native implant's base material surface will possess an inherent roughness that is largely determined by the way the bulk implant itself is manufactured and its surface finished. The oxide layer formed on or forming the dental implant surface also possesses an inherent roughness. Consequently, the overall surface roughness is a superposition of a microscale amplitude, low frequency roughness of an as-machined/finished implant surface and a nanoscale amplitude, high frequency roughness of the surface layer formed thereon. In particular in the coronal implant region the as-machined surface structure is still present/detectable at the surface and additionally "decorated" by the oxide layer. In contrast, in particular, in the apical implant region, where much thicker oxide layers can be present, as-machined surface structure of the base material is fully buried/covered by the oxide layer and does no longer significantly determine the surface properties. In case spark anodization is used to produce a surface, the formed oxide layer usually has a thickness of more than 5 μm thus masking the roughness of the as-machined surface structure.

The combination of the oxide layer thickness of 60 nm to 170 nm and the surface roughness Sa of 0.1 μm to 1.0 μm in the coronal or collar region of the dental implant, preferably a dental screw has the following advantageous biological and clinical effects. On the one hand, the specific oxide layer thickness results in an interference color of the coronal implant region that is yellow or pink when viewed by the human eye. Said coloring is beneficial to minimize grey shine-through effects through soft tissue when the dental implant is implanted. An improved soft tissue appearance can be achieved by changing the color from a metallic grey conventional encountered in the prior art to yellow or pink by deliberately adjusting the thickness of the oxide layer. Hence, the present invention could be seen as a selection invention, where from a wide range of oxide layer thicknesses potentially found in the prior art, a narrow range was deliberately selected to confer the coronal implant region with a distinct color that improves cosmetic aspects of the dental implant once implanted. In addition, the presence of an oxide layer, in particular in case of a titanium oxide layer, the coronal implant region shows good biocompatibility, stimulating adhesion, proliferation, and extracellular matrix secretion of human gingival fibroblasts. In addition, the presence of the oxide layer may confer antimicrobial surface properties. The specific minimal to moderate surface roughness can reduce peri-implant marginal bone loss as compared to smoother surfaces that are in an as-machined state. At the same time, the roughness is chosen not to be too high and thus facilitates implant maintenance, in particular improves cleanability. The biofilm or calculus formation on the surface is lower than for rougher surfaces and biofilm or calculus removal by mechanical means (brushing or the like) is significantly facilitated. In addition, as compared to much smoother surfaces, the chosen surface roughness also provides good anchorage points for tissue adhesion and integration. The specific oxide film thickness supports these effects, since ensuring that there is a stable and substantial oxide layer available in the first place.

Preferably, the surface of the coronal region is smooth, meaning it exhibits an as-machined microstructure, in particular comprising an arrangement of turning lines from the machining process, is basically non-porous and/or nanostructured. The feature "smooth" is mainly a qualitative way of describing the surface of the coronal implant region. The quantitative way is defining the surface roughness Sa as done above. "Non-porous" here means that surface of the coronal region does not exhibit a significant density or number of open pores that intersect the surface and create tiny holes thereon. Here, "pores" are defined to be holes in the surface, meaning features the diameter of which in the surface plane is much smaller than their depth perpendicular to the surface. As such, the surface is clearly distinguishable to implant surface regions that aim at strong bone tissue connection and therefore have a highly porous morphology as it will be explained below. "As-machined microstructure" here means that the surface of the coronal implant region exhibits a more or less regular "pattern" originating from the machining or the dental implants bulk. Preferably, said machining structure is preserved, still superficially detectable and not fully hidden away or buried by the superficial/superposed oxide layer. "Nanostructure" here means that the oxide layer exhibits nano-sized structures, such as recesses like golf-ball-like surface recesses, of less than 100 nm in diameter. Hence, the surface morphology of the coronal implant region is determined by both, the as-machined surface morphology and the oxide layer surface morphology. One example of such as-machined surfaces is a turned surface still exhibiting a regular pattern of fine turning lines that are covered, but not buried by the oxide layer. The pattern of turning lines leads to an "oriented" line roughness meaning that along the turning lines the line roughness would be low, but perpendicular to the turning lines it would be high due to turning lines and troughs alternating. In other words, the surface of the coronal implant region has an oriented (line) roughness. The above listed preferable features of the surface of the coronal implant region further strengthen the above advantageous effects. In other words, the surface of the coronal implant region optionally possesses both, a microstructure formed by machining, preferably in the form of a pattern of turning lines and in addition a nanostructure originating from the oxide layer formed on the as-machined surface. Said nanostructure is characterized by nanoscale indentations, recesses, spherical features and a nanoscale hill-valley structure. Said nanostructure beneficially "roughens" the otherwise very smooth (too smooth) as-machined surface thereby conferring its desired functionality, in particular good tissue integration. Said nanostructures are distinguished with respect to pores, by normally having larger diameters than depths.

The surface of the coronal region can further have an arithmetical mean height Sa in the range from 0.2 μm, preferably from 0.3 μm and further preferably from 0.4 μm to 0.4 μm, preferably to 0.6 μm and further preferably to 0.8 μm, and the oxide layer can further have an average thickness in the range from 80 nm to 130 nm, preferably to 150 nm and further preferably to 160 nm. These values are preferable surface roughness ranges and preferable oxide layer thicknesses ranges the lower and upper limits thereof are freely mutually combinable and all values in-between are part of this invention and disclosure. Also, combinations of upper limits only and lower limits only are part of this invention and disclosure. By adjusting the oxide layer thickness, it is possible to flexibly fine-tune the color and/or the nanostructures of the coronal implant region and the above biological features so as to further enhance them or adapt them to individual needs of certain indications or groups of patients.

It is preferred that the coronal region exhibits a yellow or pink color when viewed by the human eye and/or when analyzed with a spectrometer. Part of the present invention and disclosure are all colors intermediate between yellow and pink in the color spectrum. As explained above, the coloring preferably results from interference colors and reduces and minimizes grey shine-through effects through soft tissue, thus improving cosmetic and aesthetical aspect of dental implants and dental restoration technology. In the present invention and disclosure, the coloring is preferably achieved via anodization and the respective method can hence be referred to as "yellow anodization" or "pink anodization" or the like. As indicated above, the oxide layer and thus the coloring can optionally also be provided on inner surfaces of the dental implant or the component to be described below. This can contribute to better fastening of screws or the like when inserted into inner cavities having said inner surfaces.

Preferably, the dental implant according to the present invention and disclosure, further comprises a transition implant region, an apical implant region, a longitudinal axis extending from the coronal implant region to the apical implant region, wherein the sequence of regions starting from a coronal end of the dental implant to an apical end of the dental implant along the longitudinal axis is: coronal implant region—transition implant region—apical implant region, and at least one of the following applies with respect to the surface properties of said regions:

average arithmetical mean height Sa of the apical implant region>$S_a$ of the transition implant region>Sa of the coronal implant region, average developed interfacial area ratio Sdr of the apical implant region>Sdr of the transition implant region>Sdr of the coronal implant region, average thickness of an oxide layer $d_{OX}$ on the implant surface of the apical implant region>$d_{OX}$ of that of the transition implant region>$d_{OX}$ of that of the coronal implant region, and average phosphorous content $C_P$ of the oxide layer of the apical implant region>$C_P$ of that of the transition implant region>$C_P$ of that of the coronal implant region.

In principle, the coronal implant region described up to this point can be combined with any freely designed other regions of the dental implant. However, in order to provide a dental implant with overall superior properties, it is preferred to combine the coronal implant region with its advantageous properties with specifically designed other implant regions that themselves exhibit advantageous properties. In sum, this leads to a dental implant catering for a large number of design demands required to achieve an overall superior implant performance when it comes to biocompatibility and durability. Hence, it is preferred that a transition implant region exists between the coronal implant region and an apical implant region and that said two further distinct regions have distinct and purposefully designed surfaces. A preferred implant design is specified above. It can be seen therefrom that the surface properties in each of the three different regions are meant to be different. Specifically, there is a distinct evolution of physiochemical surface properties from the coronal implant region to the apical implant region with the transition implant region having intermediate property values. Hence, it is preferred that the physiochemical surface properties $S_a$, $S_{dr}$, $d_{OX}$ and $C_P$ have their lowest values/magnitudes in the coronal implant region and their highest magnitude in the apical implant region. The parameter "Sdr" called developed surface area ratio or developed interfacial area ratio is a standard parameter for surface characterization and well-known to the skilled person. It can be determined, for example, by white light interferometry using an optical 3D profilometer.

In addition, as regards a dental implant design, where different regions of the implant have differently designed surfaces, reference is made to WO 2016/096734 A1, the contents of which are incorporated herein by reference. Specifically incorporated are all teachings therein with respect to the design of the transitional region and the apical region and their surface roughness and pore sizes. Part of this invention and this disclosure is a dental implant with the above-specified colored coronal implant region in combination with any design variant of the transitional region and apical region described in said WO 2016/096734 A1. The "transitional region" in said document would then be equivalent to the "transition implant region" of this invention and the "apical region" would be equivalent to the "apical implant region".

As regards benefits and advantages of the above configuration, for example, the increase from coronal implant region to apical implant region and apex in Sdr is designed to be contrary to the bone density profile, which decreases from the implant platform to the apex. This ensures increasing friction towards the apex to allow for proper implant retention. As regards the advantages of an increasing surface roughness $S_a$ and porosity or pore sizes, reference is made to said WO 2016/096734. The advantages listed therein equally apply and unfold in the present invention.

The above introduced "longitudinal axis" is in case of a dental screw or pin-shaped, substantially cylindrical implant a central symmetry axis, e.g., the shaft axis of the dental screw extending along the major axis (length axis) of the dental implant, along which the coronal and apical region are situated. Assuming that the dental implant has an aspect ratio corresponding to its length being distinguishably larger than its width (diameter), then the longitudinal axis is the length axis.

The above phosphorous content $C_P$ is linked to the oxide layer, i.e., is an oxide layer property and measured on and from its surface. The phosphorous may originate from the process with which the oxide layer is produced. If this is done by anodic oxidation, then phosphorous found in the electrolyte used is incorporated into the oxide layer. Specifically, the phosphorous content and the surface chemistry can be determined using X-ray photoelectron spectroscopy (XPS) or any other suitable method known to the skilled person. Having phosphorus in the superficial oxide layer, preferably in the form of phosphates, enhances osteoblastic cell attachment and differentiation with a high potential for improving bone healing. Phosphorous enhances osseointegration. It is conceivable that the presence of phosphorous, which is also a constituent of bone apatite, further stimulates bone tissue integration of the dental implant, in particular when present in the apical implant region. Hence, having the highest phosphorous content there is particularly preferred.

The surface properties, specifically the physiochemical surface properties of the apical implant region, the transition implant region and the coronal implant region may change in a stepwise manner or a continuous/smooth manner, preferably a gradient manner, or combinations thereof between the different regions along the longitudinal axis of the dental implant. The above lists a number of design options how the in surface properties evolution along the dental implant can be realized. On the one hand, some or all of the surface properties can either change incrementally along the longitudinal axis of the dental implant or change abruptly within a few micrometers along the longitudinal axis. Each of the surface properties can have its very own variation profile along the longitudinal axis. In particular, non-correlated surface properties can vary independently from each other and can exhibit very different variation profiles. Having a continuous, smooth or gradient change increases the in-use flexibility of the dental implant, since no spatially discrete step change in implant surface characteristics occurs, which would require a more precise placement during implantation. Further, consequences of in-vivo changes like bone atrophy are better moderated by the continuous change in surface properties as compared to implants with abrupt and significant changes. However, stepwise changes can be advantageous in controlled implantation scenarios, where sharp tissue interfaces exist and hence a sharp transition in surface properties is desired.

Preferably, in the apical implant region, the transition implant region and/or the coronal implant region, the oxide layer further comprises calcium, magnesium and/or fluoride.

Given that said elements are also constituents of bone apatite, it is conceivable that their presence further stimulates bone tissue integration of the dental implant, in particular when present in the apical implant region. The incorporation of elements in the oxide layer, via ion implantation or doping can improve biological performance of metallic surfaces. Part of the present invention and disclosure is thus the modification and functionalization of the oxide layer via incorporation of elements and/or substances therein that are not normally part of the oxide layer. Hence, the oxide layer may be an ion-implanted, ion-exchanged, doped, coated and/or functionalized one.

Optionally the surface of the apical implant region and the transition implant region are microporous surfaces and/or comprise at least one of a bone-growth-initiating and a bone-growth-stimulating substance. Said substances are preferably of the superfamily TGF-beta. Thereby, bone tissue integration can be purposefully and actively improved by stimulating bone cell proliferation and in-growth.

In a specific preferred embodiment of the dental implant, the surface of the apical implant region exhibits at least one, preferably all of:

- average Sa: 1.50 μm±0.4 μm,
- average Sdr: 187%±50%,
- mean pore diameter: 1.5 μm±0.5 μm,
- average oxide layer thickness $d_{OX}$: 9000 nm±3000 nm, and
- average phosphorus content $C_P$: in a range from 4%, preferably from 6% to 10%, preferably to 12%, and/or the surface of the transition implant region exhibits at least one, preferably all of:
- average Sa: 0.8 μm±0.5 μm preferably ±0.3 μm,
- average Sdr: 148%±40%,
- mean pore diameter: 1.0 μm±0.5 μm
- average oxide layer thickness $d_{OX}$: 7000 nm±3000 nm, and
- average phosphorus content $C_P$: in a range from 3%, preferably from 5% to 9%, preferably to 11%, and/or the surface of the coronal implant region exhibits at least one, preferably all of:
- average Sa: 0.5 μm±0.3 μm,
- average Sdr: 16.6%±15%,
- mean Nanostructure size: 80 nm±50 nm,
- average oxide layer thickness $d_{OX}$: 120.0 nm±40 nm, and
- average phosphorus content $C_P$: in a range from 2%, preferably from 3% to 5%, preferably to 6%.

The above "±" (+/−) values and the ones used later in this description are meant to indicate possible ranges in which the physiochemical surface parameters may vary and not error margins of the measurements. The so created ranges and their boundary values are meant to be combinable with other ranges boundary values of the present invention and disclosures. Also, all intermediate values are meant to be embraced.

Preferably, the surface properties of the apical implant region, the transition implant region and the coronal implant region are at least partially obtainable, preferably obtained by performing an anodic oxidation process, preferably wherein the surfaces of said regions are anodized surfaces comprising the oxide layer. Said method is known for providing a high degree of flexibility in producing and designing superficial oxide layers of high durability. Alternatively, sand-blasting or acid-etching can be used to produce the oxide layer for this invention.

The surfaces of the transition implant region and/or the apical implant region are obtainable, preferably obtained by a spark anodization process. This process is a variant of anodic oxidation, where high voltages are used to create sparks. A so processed surface is comparably rough and shows many open pores, has a high open porosity and crater/volcano-like structure. Using spark anodization is a way of roughening and structuring the implant surface. This is beneficial for osseointegration and provides surface features for bone tissue to grow into and attach thus retaining the implant in the bone.

It is further preferred that the base material of the dental implant comprises, preferably consists of titanium or a titanium alloy and optionally that the oxide layer on the surface of the apical implant region and the transition implant region comprises crystalline titanium oxide in the anatase phase, preferably in the range of 70-100% and the remainder comprises rutile and/or amorphous titanium oxide. Using a titanium material as the dental implant base material is beneficial in that titanium and its alloys are widely studied and well known biomaterial with proven high biocompatibility and suitable mechanical properties. The preferred anatase fraction contributes to the good biocompatibility of the dental implant and promotes pronounced bone tissue integration in particular in the apical implant region.

Optionally and in contrast to the transition implant region and the apical implant region, the oxide layer of and on the surface of the coronal implant region comprises predominantly or consists fully of amorphous titanium oxide. Further preferably, the oxide layer of the coronal implant region and further the surface of the coronal region is virtually non-crystalline and/or anatase-free. Being virtually non-crystalline and/or anatase-free means that by means of X-Ray diffraction, for example, grazing incidence X-Ray diffraction, no statistically meaningful signals for crystal phases and/or anatase are detected.

In the dental implant according to a preferred embodiment of the present invention, the coronal implant region extends from a coronal end of the dental implant up to 2 mm±0.5 mm along the longitudinal axis towards an apical end of the dental implant, the transition implant region extends from said 2 mm±0.5 mm up to 4 mm±0.5 mm further along the longitudinal axis towards the apical end of the dental implant, and the apical implant region extends from said 4 mm±0.5 mm up to the apical end of the dental implant. The aforementioned is basically a definition of the spatial extend of the different implant regions along the dental implant, specifically along its length or longitudinal axis as defined above. Consequently, the coronal implant region may have a length of about 2 mm beginning from the coronal end of the dental implant. The transition region can also have an approximate length of 2 mm and starts from 2 mm away from the coronal end of the dental implant and ends about 4 mm away therefrom adjacent to the apical implant region. The apical implant region follows the transition region and starts from about 4 mm away from the coronal end of the dental implant and extends up to and includes the apical end/apex of the dental implant. Alternatively, the coronal implant region has a length measured from a coronal end of the dental implant along the longitudinal axis towards an apical end of the dental implant from 0.5 mm, preferably 1.0 mm, more preferably 1.5 mm to 2.5 mm, preferably to 4.0 mm and more preferably to 6.0 mm. As can be seen from this embodiment, the coronal implant region is not limited to a length of about 2 mm, but can be longer and thus extends further from the coronal end of the dental implant along the longitudinal axis towards the apical end/apex of the dental implant. These options confer great flexibility in designing the dental implant surface with respect to the specifics of implantation scenarios and patient needs. For example, for long dental implants, it may be preferred that also the coronal implant region is longer. The same may apply to case, where the in-situ and in-vivo conditions require a larger/longer region of yellow color and/or increased cleanability.

Component

A further aspect of the present invention and disclosure is a component for dental applications or dental component, preferably a dental abutment, wherein the surface of the component is at least partly, preferably fully, covered by an oxide layer with an average thickness in the range from 60 nm to 170 nm and an average arithmetical mean height Sa in the range from 0.05 µm to 0.5 µm.

The generic term "component" used here is meant to embrace parts and devices for dentistry other than the aforementioned dental implant. Hence, preferably, the dental implant and the component are different entities. In a preferred embodiment, the component is hence a dental component yet further preferred a dental abutment or dental implant abutment. Conventionally in dentistry, "abutment" is construed to be a separate entity used to mediate a connection between a dental implant and a dental restoration. Such conventionally understood part is embraced by this invention and disclosure. Hence, the component may be a dental abutment as typically understood by the skilled person.

It can be appreciated from the above, that the surface of the component is meant to be very similar to that of the coronal implant region of the dental implant described above, with the Sa range being somewhat narrower and shifted to lower values. Nevertheless, all explanations and definitions given above with respect to the coronal implant region do apply mutatis mutandis to the component. Hence, for the sake of conciseness of this specification, they are not repeated here explicitly, but do apply respectively. This also explicitly applies to all of the optional component features described below that find a respective counterpart in the optional dental implant features. Vice versa, explanations given for optional component features may apply to respective dental implant features outlined above. The intended resemblance between the surface of the coronal implant region and the surface of the component (abutment) means that all preferred and optional features described above for the coronal implant region (e.g., Ca, Mg, F content; non-crystalline, anatase-free etc.) can also be applied to the surface of the abutment, even, if said features are not explicitly repeated here.

The above component and its surface design is advantageous in that it supports soft tissue attachment, minimizes bacteria accumulations and also minimizes grey shine-through effects through soft tissue. The specific surface roughness Sa limits plaque formation and favors a stable soft tissue seal. The presence of an oxide layer supports epithelial cell attachment.

Preferably, the surface of the component is at least partially obtained by performing an anodic oxidation process, preferably wherein the surface of the component is an anodized surface comprising the oxide layer. Again, reference is made to the explanations provided for the respective feature of the coronal implant region, which do apply here. In particular in case of the abutment base material being titanium or a titanium alloy, which is an embodiment of this invention, anodic oxidation may endow the titanium surface with antimicrobial properties, thus reducing bacteria accumulation. Further, oxidized nanostructured titanium surfaces according to one embodiment of this invention stimulate adhesion, proliferation, and extracellular matrix secretion of human gingival fibroblasts compared to as-machined surfaces. The abutment surface may also be obtained by acid-etching and/or sand-blasting, which are both included in this invention. Preferably, the oxide layer on the surface of the component is virtually non-crystalline and/or anatase-free. Being virtually non-crystalline and/or anatase-free means that by means of X-Ray diffraction, for example, grazing incidence X-Ray diffraction, no statistically meaningful signals for crystal phases and/or anatase are detected.

In a further embodiment, the surface of the component is smooth, nanostructured, basically non-porous and/or exhibits an as-machined structure, in particular comprising an arrangement of turning lines from the machining process. Thereby, the same advantageous surface structure, effects are obtained as described and explained above for the dental implant, in particular its coronal implant region.

Preferably, the surface of the abutment exhibits a yellow or pink color when viewed by the human eye and/or when analyzed with a spectrometer. Said color also is an interference color caused by the oxide layer on the component's surface. The color can be tuned by varying the thickness of the oxide layer, thus minimizing grey shine-through effects through soft tissue and improving in-situ appearance. In the present invention and disclosure, the coloring is preferably achieved via anodization and the respective method can hence be referred to as "yellow anodization" or "pink anodization" or the like. As indicated above, the oxide layer and thus the coloring can optionally also be provided on inner surfaces of the dental implant or the component to be described below. This can contribute to better fastening of screws or the like when inserted into inner cavities having said inner surfaces.

Optionally, the surface of the component has an average arithmetical mean height Sa in the range from 0.08 μm, preferably from 0.13 μm to 0.3 μm, and further optionally wherein the oxide layer has an average thickness in the range from 80 nm to 130 nm, preferably to 150 nm and further preferably to 160 nm. Said narrower ranges further enhance the beneficial effects as outlined above and for the similarly designed coronal implant region. The preferred numerical values can be mutually combined and every conceivable combination is embraced by this invention and disclosure.

In a particularly preferred embodiment, the surface of the component exhibits at least one, preferably all of:
  average Sa: 0.2 μm±0.1 μm,
  average Sdr: 5.0%±5%,
  mean nanostructure size: 80 nm±50 nm,
  average oxide layer thickness $d_{OX}$: 120 nm±40 nm, and
  average phosphorus content $C_P$: in a range from 2%, preferably from 3% to 5%, preferably 6%.

The above "±" (+/−) values and the ones used later in this description are meant to indicate possible ranges in which the physiochemical surface parameters may vary and not error margins of the measurements. The so created ranges and their boundary values are meant to be combinable with other ranges boundary values of the present invention and disclosures. Also, all intermediate values are meant to be embraced.

As indicated earlier, the base or bulk material of the component comprises, preferably consists of titanium or a titanium alloy, for the same reasons and benefits as explained for the coronal region of the dental implant. First of all, since titanium-based material are well-known and widely-used biomaterials. Using such materials is in particular beneficial when anodic oxidation/anodization is used, leading to a highly functional and useful titanium oxide layer on the component's surface.

Implant System

A yet further aspect of the present invention and disclosure is an implant system comprising or consisting of the dental implant as defined and specified above, and the component also as defined and specified above. An innovative implant system was engineered with surfaces designed based on the biological and clinical needs and ensuing design input. The dental implant and the component are configured to be connectable to each other. In particular in case where the component is a dental abutment, the skilled person will appreciate that the dental implant and dental abutment are mutually designed so as to be combinable and connectable to each other. Said two parts then complement each other and form an assembly. Often, the dental implant has a female geometry (bore, recess or the like) in which a male geometry of the dental abutment is insertable. Inverse geometries or screw or glue connections or the like are also possible and embraced by this invention and disclosure. The above system hence combines all the benefits and advantages outlined above for each separate component into one assembly, thereby obtaining a novel implant system with overall superior properties. The dental implant and component with the specifically designed surfaces were tested for cell adhesion and proliferation, and healthy cell adhesion and proliferation when seeded on the optimized design were confirmed.

Also part of this invention and disclosure is a kit-of-parts, meaning a loose provision of the dental implant and the component, for example, ready-for-use in a sterile pouch or bag. Said kit may be supplemented by the dental restoration part described further below so as to form a three component kit-of-parts.

It is preferred that the surface morphologies and/or the magnitudes of individual surface properties, i.e., physico-chemical properties, of the coronal implant region and of the component resemble each other. In other words, part of this invention and disclosure is an assembly or kit-of-parts, where the dental implant and the component, preferably a dental abutment, are matched with each other regarding their surface properties. "Matching" preferably implies that the surface of the coronal implant region is more similar to the surface of the component than the surface of any one of the other regions, the transition implant region or the apical implant region. The similarity/resemblance in surface texture, chemical composition, oxide layer thickness and nano-structures between the component surface and the coronal implant region allows for a smooth soft tissue transition from the component/abutment to the dental implant.

Expressed differently, preferably the difference of the magnitude or value of individual surface properties of the coronal implant region and of the component is smaller than the difference of the magnitude or value of individual surface properties of the apical or transition implant region and the coronal implant region.

For example when a dental implant is used the surface of which coronal implant region exhibits at least one, preferably all of:
  average Sa: 0.5 μm±0.3 μm,
  average Sdr: 16.6%±15%,
  mean Nanostructure size: 80 nm±50 nm,
  average oxide layer thickness $d_{OX}$: 120.0 nm±40 nm, and
  average phosphorus content $C_P$: in a range from 2%, preferably from 3% to 5%, preferably to 6%, then an component (dental implant) is combined therewith the surface of which exhibits at least one, preferably all of:

average Sa: 0.2 µm±0.1 µm, average Sdr: 5.0%±5%, mean nanostructure size: 80 nm±50 nm, average oxide layer thickness $d_{OX}$: 120 nm±40 nm, and average phosphorus content $C_P$: in a range from 2%, preferably from 3% to 5%, preferably 6%.

Once again, the above "±" (+/−) values and the ones used later in this description are meant to indicate possible ranges in which the physiochemical surface parameters may vary and not error margins of the measurements. The so created ranges and their boundary values are meant to be combinable with other ranges boundary values of the present invention and disclosures. Also, all intermediate values are meant to be embraced.

One preferred option for the implant system is a combination, where the dental implant is made of technically pure titanium and the component (abutment) is made of a titanium alloy.

In a preferred embodiment, the implant system further comprises a dental restoration element, wherein the implant, the component and the dental restoration element are combined and connected and form an assembly. Optionally, said three components form a dental kit-of-parts. The dental restoration element can be a crown or the like. The present invention and disclosure thus embraces a complete system for replacing teeth via dental implantology that has superior properties, specifically originating from the surface of designed and matched dental implant and component.

As regards possible ways of producing the above described dental implant in particular the surfaces of the transition implant region and the apical implant region, reference is made to the methods of modifying an implant's surface in the publications WO 00/72777 A1 and Wo 01/76653 A1, which can also be employed to produce the dental implant according to the present invention, in particular, for embodiments where the dental implant or component comprises or consists of titanium or a titanium alloy. Preferably, the surfaces are hence produced by anodic oxidation and spark anodization, with which the surface of the as-machined implant is transformed into one with an oxide layer thereon. Spark anodization, i.e., anodic oxidation with high voltages, produces a rough surface with many crate-like features as it is desired for the apical implant region. Electrolytes usable for the anodic oxidation/anodization are diluted $H_2SO_4$ and $H_3PO_4$, heated acids or salt baths. Typical voltages for the anodic oxidation/anodization, in particular for producing the surface of the coronal region of the dental implant and the surface of the component, range from 30 V to 100 V, preferably 55 V to 80 V. Typical anodization durations/times range from 20 s to 90 s, preferably 30 s to 70 s. Spark anodization used in particular to produce the surface of the apical implant region is carried out with voltages on the range of 240 V to 300 V.

BRIEF DESCRIPTION OF THE DRAWINGS

The drawings presented below are exemplary, non-limiting schematic drawings only.

FIGS. 3A, 3B, 3C, 3D, 3E, 3F, 3G, 3H, 3I, 3J, 3K, 3L, and 3M show an implant system consisting of dental implant and dental abutment according to the present invention and disclosure together with microscopy images illustrating the surface properties and morphologies for each part of the system.

FIG. 4A shows on the left a state in which the protective layer is formed on an implant surface. Atmospheric molecules, such as water and hydrocarbons, are unable to reach the surface, as the protective layer provides a physical barrier.

Figures 4A, 4B, 4C, 4D, 4E, 4F:
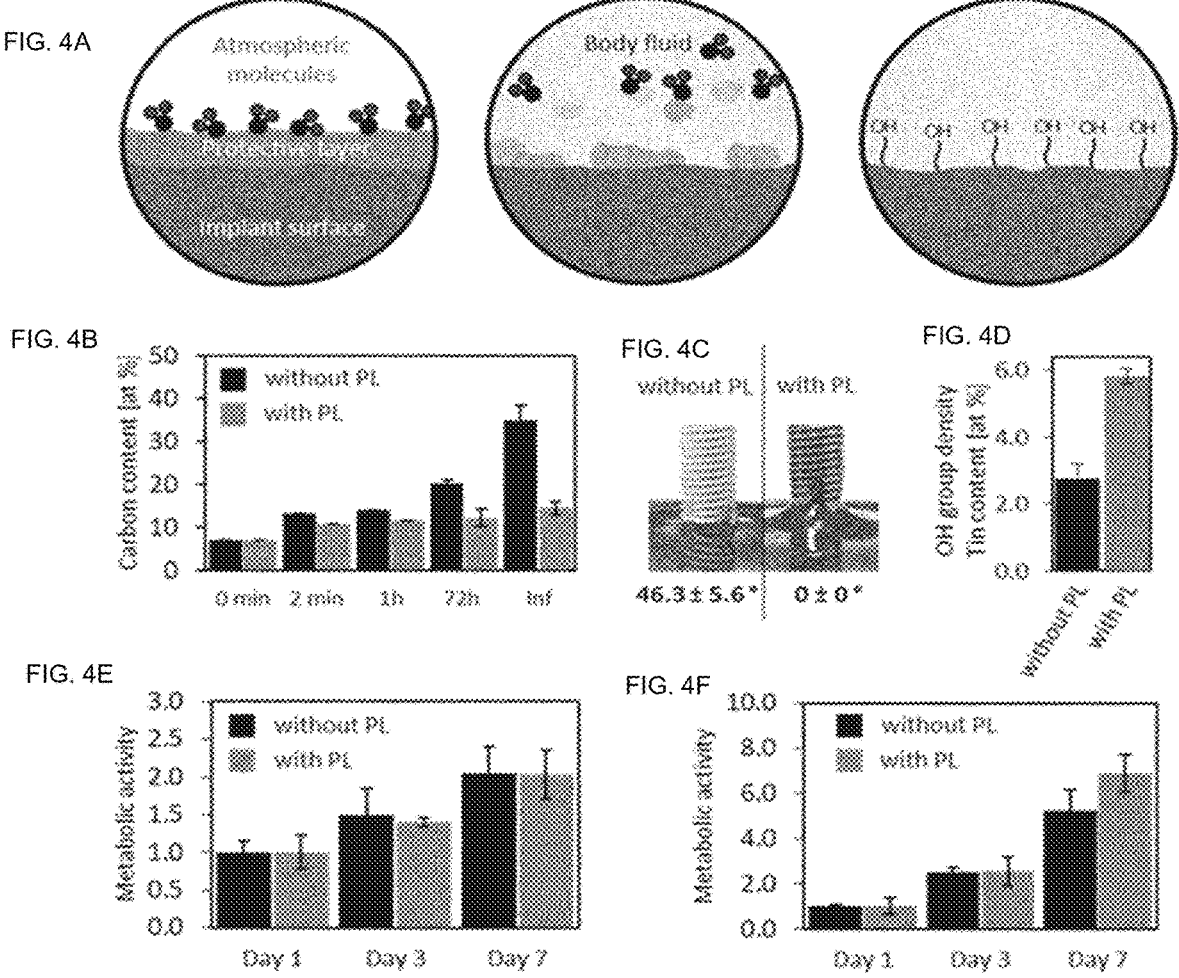
FIGS. 4A, 4B, 4C, 4D, 4E, and 4F show an illustration of surface properties and functionalities of the implantable or implant component related to using a protective layer according to the present invention. Herein, the implantable or implant component is represented by an implant.

In the middle of FIG. 4A, it is shown how upon contact with body fluid, the protective layer dissolves or disintegrates rapidly. Any molecules that are adsorbed from the air are carried away while the protective layer dissolves or disintegrates.

On the right side of FIG. 4A, there is illustrated a state of the implant after the protective layer has dissolved or disintegrated to allow interaction of the implantable or implant component with the surrounding tissue. Note that in this exemplary embodiment, the implantable or implant component is made from a material that has hydroxyl groups (OH) on the surface, such as titanium, which indicates a highly hydrophilic surface (water droplet contact angle e.g. in the range of from 0-30°).

FIG. 4B shows the content of carbon, derived from hydrocarbons that are adsorbed from the surrounding atmosphere, on the surface of implants with and without protective layer (PL) after certain time periods.

In FIG. 4C, there is illustrated a contact angle measurement on implants having a contact angle of 46.3° (without PL, left) and 0° (with PL, right).

FIG. 4D illustrates the density of hydroxyl groups on a titanium surface that had not been protected by a PL (left) and on the surface of titanium surface that had been protected by a PL.

FIGS. 4E and 4F show the metabolic activity after 1, 3 and 7 days on implants that were (with PL) or were not (without PL) provided with a protective layer of the present invention.

DETAILED DESCRIPTION

The working examples detailed below are meant to be non-limiting. The invention and the above disclosure are not limited to the details of the below working examples, which only describe a preferred way of implementing the present invention.

Figures 1A, 1B, 1C:
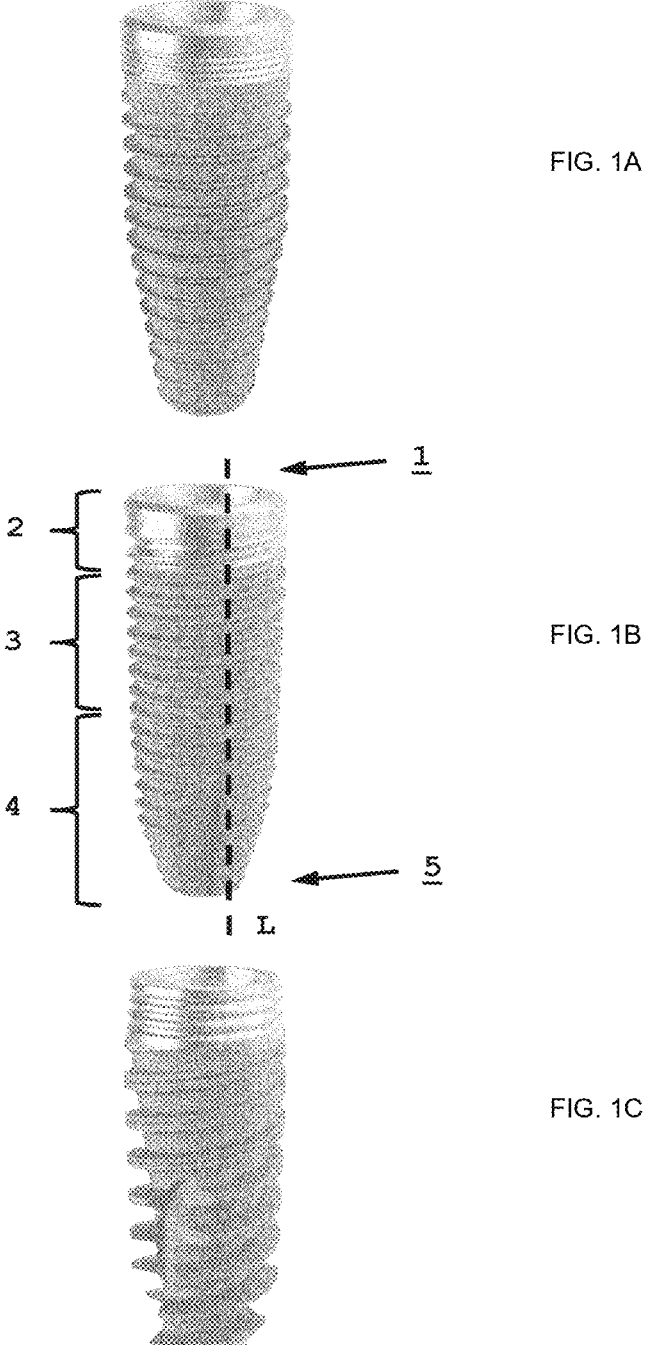
FIGS. 1A, 1B, and 1C show a collection of dental implant designs according to the present invention and disclosure.

FIGS. 1A-1C show a number of different designs of the dental implant according to the present invention and disclosure. As can be seen, the dental implant can be screw-like or a bone screw for insertion into the jaw bone. Various different thread-designs are conceivable, for example, one thread type extending from the apical end to the coronal end of the dental implant. The thread types may also be varied along the longitudinal axis and different threads can be provided in different implant regions. For example, the thread in the apical region is different to the one in the coronal region thereby accommodating different retention needs in the different tissues the dental implant intersects. Other retaining means than threads are also possible, for example, a regular ridge structure with ridges perpendicular to the longitudinal axis. Also the length and longitudinal extent of the different regions of the dental implant can be different. In FIGS. 1A-1C, the length of the coronal region is about 1/7 to 1/8 of the total length of the implant measured from the coronal end of the dental implant. FIGS. 1A-1C indicate via the lighter color that the coronal or collar implant region has a distinctively different appearance than the rest of the dental implant, which is due to the different surface designs. Seen in color, the coronal implant region would exhibit a gold color, i.e., a metallic yellow color, whereas pink is also conceivable. The rest of the implant however would be matt grey. In the present example, the transition to the coronal region is substantially abrupt on a scale visible by the human eye. Exemplarily, FIG. 1B contains reference numerals that also apply to the dental implants in FIGS. 1A and 1C. Indicated in FIG. 1B is the longitudinal axis L of the dental implant, which is the lengthwise spatial extension of the dental implant. The upper end of the dental implant is formed by the coronal end 1. The apex or lower end of the dental implant is formed by the apical end 5. The three different regions: coronal implant region 2, transition implant region 3 and apical implant region 4 are indicated accordingly, but not limited to the ranges indicated therein.

Figure 2A:
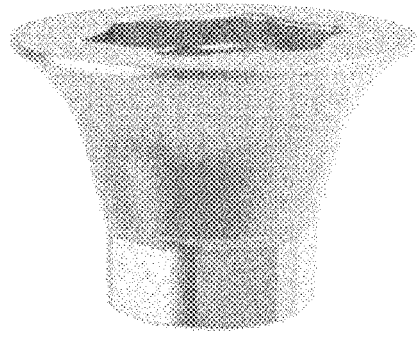
FIGS. 2A and 2B show a collection of component designs in the form of dental abutments in line with the present invention and disclosure.
Figure 2B:
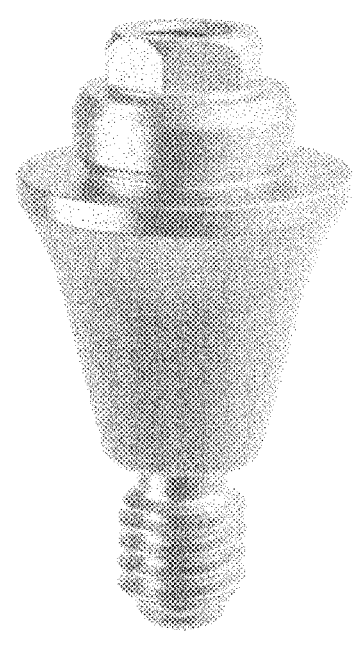

FIGS. 2A and 2B depict two design options for the component, here in the form of abutments to be used together with dental implants. At the lower ends thereof, one can see geometries provided for combination and connection with a suitable dental implant. When seen in color, the abutments would have a gold color or metallic yellow color depending on the individual part of the abutment glossy or matt.

FIGS. 3A-3M show the implant system according to the present invention, where a respective dental implant of a screw-type is combined with a respective component in the form of a dental abutment. FIGS. 3B, 3C, 3E, 3F, 3H, 3I, 3K, and 3L show scanning electron microscopy images at different magnifications. The apical or apex implant region shows a pronounced crater/volcano structure with open pores on the surface reaching opening sizes up to several micrometers. The surface is ragged and comprises a large number of randomly distributed surface structures. The adjacent transition implant region shows a similar crate/volcano and ragged morphology. However, the surface features and pores have become smaller. A significant change occurs in the coronal implant region, where the porous and ragged surface is gone and instead a regular pattern of lines or grooves can be seen, which come from the turning process. Said lines and grooves confer the surface with an oriented line roughness. In higher magnification, one discovers a finely nanostructure surface. Here, the oxide layer basically "decorates" and covers the turning line structure. Finally, turning to the dental abutment, one can see that in the depicted embodiment that the surface morphology of the dental abutment is very similar to that of the coronal implant region, showing an array of turning lines/grooves with a superimposed oxide layer. FIGS. 3D, 3G, 3J, and 3M show 3D reconstructions of surface profiles obtained by white light interferometry that confirm the above observations.

Figure 3A:
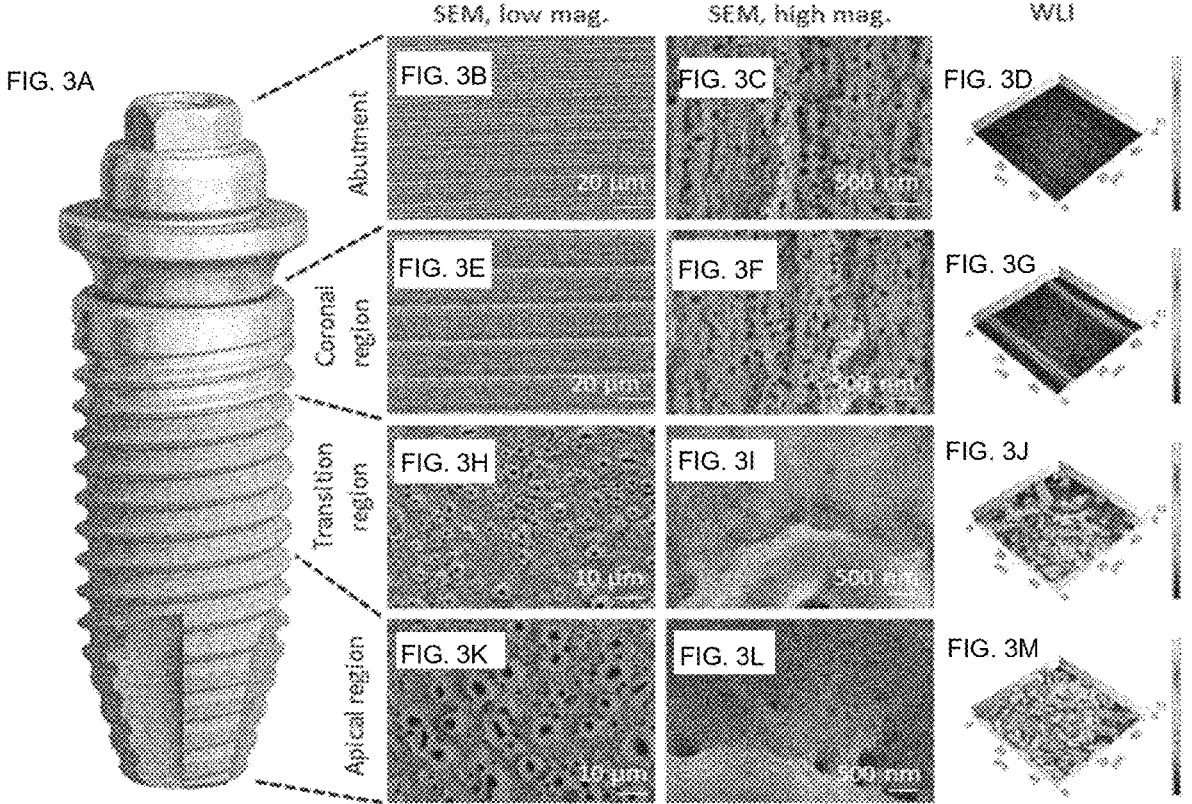

Regarding the example shown in FIGS. 3A-3M, the following can be detailed. The novel abutment surface was prepared by turning followed by a mild anodization process. The resulting surface is non-porous, smooth with an average surface roughness Sa of $0.13\pm0.02$ µm and a developed surface area ratio Sdr of 3.39% (see: FIGS. 3B and 3D), shows regularly distributed nanostructures of $69\pm48$ nm in size and has an oxide layer thickness of $153\pm5$ nm (see: FIG. 3C). The oxide layer thickness endows the abutment with a yellow color—known as interference color—which has been shown to be beneficial to reduce grey shine-through effects in case of a thin mucosa. Due to the created nanostructures and the approximately 20 times increase in oxide layer thickness compared to unmodified titanium, the created surface should be favorable for epithelial cell and fibroblast attachment. Moreover, the smooth surface is expected to allow for control of plaque retention and facilitate mechanical cleaning. The collar or coronal region of the dental implant (0-2 mm from the coronal end) has a minimal roughness with a Sa of $0.51\pm0.03$ µm and a Sdr of 16.6%. The roughness is obtained by control of the machining parameters resulting in burr-less surfaces with defined turning line dimensions and spacing, as visible in FIGS. 3B and 3D. Additionally, the coronal implant region features similar nanostructures like the abutment $43\pm21$ nm in size and an oxide layer thickness of $142\pm17$ nm (see: FIG. 3F). Minimally rough surfaces with a Sa of 0.5-1.0 µm have shown less marginal bone loss compared to smoother surfaces. The herein created surface roughness for the implant collar/coronal implant region should thus be at a reasonable level to balance the need for osseointegration and the need for maintenance and cleaning. Moreover, the similarity in surface texture, chemical composition, oxide layer thickness and nanostructures between the abutment surface and the coronal implant region allows for a smooth soft tissue transition from the abutment to the implant as mentioned before. The body of the implant is gradually roughened by spark anodization. By varying the density and size of the classical volcano-shape saliencies on the surface, the roughness increases from Sa of $0.92\pm0.16$ µm in the transition implant zone (i.e. 2-4 mm from the coronal end of the dental implant) to a Sa $1.49\pm0.19$ µm in the apex area/apical implant region (4 mm-apex), closely approaching the roughness known to trigger the best bone response in vivo. The increase in roughness from the transition implant region to the apical implant region is also accompanied by an increase in surface area as reflected in the Sdr values of 148% and 187%, respectively. Overall, the increase from coronal end to apical end in Sdr is designed to be contrary to the bone density, which decreases from the implant platform/coronal end to the apex and apical end. This ensures increasing friction towards the apex to allow for proper implant retention. The high currents exceeding the breakdown voltage used for roughening the surface of the transition and/or apex implant region, lead to the formation of oxide layer two orders of magnitude higher, reaching $7.2\pm0.3$ µm and $9.9\pm1.3$ µm for the transition and apical implant region, respectively. These oxide layers are anatase-rich with a high surface energy and many free hydroxyl groups. Compared to sand-blasted and acid-etched commercial implants, anodized surfaces exhibit the most hydroxyl groups. Highly hydroxylated titanium surfaces promote osseointegration and bone formation in vivo, likely through a favorable adsorption of ECM molecules and enhance mineralization and differentiation of osteoblasts. Anatase rich anodized implant regions possess optimized properties for osseointegration resulting in a high treatment predictability of a variety of indications and in lower failure rates than other surface modifications after more than 10 years of function. During the growth, oxygen and phosphorus from the electrolyte are incorporated into the oxide layer. The abutment surface exhibits on average $3.49\pm0.36$% phosphorus, while the surface of the coronal implant region shows $4.00\pm0.13$%, the transition implant region $7.20\pm0.59$% and the apical implant region $8.16\pm0.31$%. The table below summarizes the physiochemical surface properties for the various components and regions of the above implant system.

TABLE 1

| | Component (Abutment) | Dental Implant | | |
| --- | --- | --- | --- | --- |
| | | Coronal region 0-2 mm | Transition region 2-4 mm | Apical region 4 mm-Apex |
| Average Sa [μm] | 0.13 ± 0.02 | 0.49 ± 0.03 | 0.92 ± 0.16 | 1.49 ± 0.19 |
| Average Sdr [%] | 3.39 | 16.6 | 148 | 187 |
| Average pore diameter [μm] | non-porous | non-porous | 1.1 ± 0.5 | 1.7 ± 1.1 |
| Average Nanostructure size [nm] | 69 ± 48 | 43 ± 21 | Not nano-structured | not nano-structured |
| Average oxide layer thickness on the surface [nm] | 153 ± 5 | 142 ± 17 | 7227 ± 305 | 9933 ± 1286 |
| Average phosphorus content on the surface | 3.49 ± 0.36% | 4.00 ± 0.13% | 7.20 ± 0.59% | 8.16 ± 0.31% |

In the following, the measurement methods used to determine the above physiochemical properties will be explained. Said methods also provide examples for relevant measurement methods generally applicable in order to determine all the parameters mentioned in this description.

Oxide Layer Thickness $d_{OX}$

Said thickness is measured on cross-sections of the dental implant or the component. For that, the dental implant or component can be cold mounted in an acrylic resin, ground and polished to achieve cross sections along its centerline or its longitudinal axis (which will be defined below). The flank of the dental implant or component can be imaged by scanning electron microscopy (SEM) and the oxide layer thickness measured software-aided in said SEM images at various positions, which is a procedure well familiar to the skilled person. For the measurements made here, a Zeiss Leo 1530 scanning electron microscope, a secondary electron detector and 5 kV acceleration voltage at various magnifications were used. Pore diameter and nanostructures were determined using the ImageJ software and SEM images with a magnification of 1 k and 10 k respectively. 6 images were used for each condition. Preferably, the above thickness of the oxide layer is an average thickness, meaning that it was measured at various position of the coronal implant region or any implant region of relevance and then the mathematical average calculated from all of the measurements.

Roughness Parameters Sa and Sdr

Were measured using white light interferometry. Image stacks of the implant surface were acquired with an Optical 3D Profilometer, gbs, smart WLI extended (Gesellschaft für Bild and Signalverarbeitung mbH, Ilmenau, Germany) using a 50× objective. The data obtained was subsequently processed with the MountainsMap® software for determination of the surface roughness. Parameters Sa and Sdr were determined after applying a polynomial 3 removal form and a Gaussian filter (FALG, ISO 16610-61) with a 50 μm cut-off. The measuring area was 350×220 μm for all measurements. Four components and 4 dental implants were measured, the dental implants were measured on 9 areas each for each region depicted in FIGS. 3A-3M, i.e., coronal, transition and apical regions. The abutments were measured on 9 areas each.

Phosphorus Content CP and Surface Chemistry

For determining the elemental composition of the surfaces X-ray photoelectron spectroscopy (XPS) measurements were performed with the following procedure. Samples were rinsed two times 120 s in 10 mL ultrapure water (type 1, 18.2 MΩ·cm resistivity). The samples were then dried with a stream of nitrogen gas and mounted on a XPS sample holder.

Care was taken to expose the cleaned implants for the minimal amount of time to the laboratory atmosphere. XPS measurements were performed with a Kratos Axis Ultra spectrometer using monochromatic Al Kα X-rays (1486.6 eV). Binding energy calibration of the Kratos Axis Ultra DLD XPS instrument, S/N C332549/01 was carried out on 18, Jul. 2018, according to BS ISO 15472:2010. For each sample, a survey spectrum was acquired from an area of ~2 mm×~1 mm (pass energy=160 eV), from which the surface elemental composition was determined. Charge compensation was achieved using a beam of magnetically focused electrons as a flood current. The standard photoelectron take-off angle used for analysis is 90° giving a sampling depth in the range 5-8 nm.

Pore Diameter and Nanostructure Size

Were determined based on SEM images of the respective surfaces. Conventional image software was used to measure pore sizes and nanostructure sizes.

Method for forming a protective layer, Use and Implant or implantable component having a protective layer.

The present inventors have surprisingly found that the surface of an implantable or implant component can be protected during storage e.g. against contamination by providing a protective layer formed from a solution having a relatively low pH as described below. Such a protective layer can be more quickly and more completely be removed as compared to layers formed in the prior art, and/or can provide or maintain a surface state of the implantable or implant component that is preferable for biointegration.

In one aspect, the present invention relates to a method for forming a protective layer on the surface of an implantable or implant component, the method comprising a) applying a solution on the surface of component, the solution having a pH at 25° C. of 6.8 or less;

b) drying the solution applied in step a) to form a protective layer on the surface of the implantable or implant component.

Herein and throughout the present invention, the term "solution" denotes a composition that is in a liquid state at 20° C. and 1 atm pressure.

In one embodiment, the solution comprises inorganic cations and inorganic anions in a solvated (dissolved) state. In the present invention, the terms "inorganic cation" and "inorganic anion", respectively, denote charged species of an element or an element group that together form a salt. Examples of inorganic cations are cations of the alkaline metals, the earth alkaline metals, and any other metal. The term however also includes ammonium and cations of e.g. Boron, Arsenic, Tellurium, etc., Put differently, an "inorganic cation" can be described as including any positively charged species not containing carbon.

The term "inorganic anion" includes any negatively charged species not containing a carbon atom. In one embodiment, the term "inorganic anion" includes the anions of the halogens (in particular F, Cl, Br, I), anions containing nitrogen and oxygen atoms, such as nitrate or nitrite, anions containing nitrogen and oxygen atoms, such as sulfate or sulfite, and anions containing phosphorous and oxygen atoms, such as phosphate, pyrophosphate, or phosphite. Incidentally, in the present invention ions that are formed by dissociation of water (i.e. $H^+/H_3O^+$ and $OH^-$) are not included in the terms "inorganic cation" and "inorganic anion", respectively.

The term "monovalent", "bivalent" and "trivalent" denote the charge of a cation or anion. Examples of monovalent cations are those of the alkali metals such as $Na^+$ or $K^+$ and ammonium, and examples of monovalent anions include $Cl^-$ and $H_2PO_4^-$. Examples of bivalent cations include those of the earth alkaline metals, such as $Ca^{2+}$ and $Mg^{2+}$, and examples of bivalent anions include e.g. $SO_4^{2-}$ and $HPO_4^{2-}$. Examples of trivalent anions include e.g. $PO_4^{3-}$.

The solution may be an aqueous solution. Herein, the term "aqueous" denotes that the solution comprises 50% by weight of the total composition or more of water, such as 70% by weight or more or 80% or more, such as 90% by weight or more. Other co-solvents that may optionally be present in addition to water include water-miscible solvents, in particular alcohols and ketones such as methanol, ethanol, isopropanol, 1-butanol, 2-butanol, or acetone. These co-solvents are typically present in an amount of less than 50% by weight of the total weight of the composition, such as 30% by weight or less or 20% by weight or less.

The solution may also be a non-aqueous solution. This denotes a solution that does not comprise water or comprises it in an amount of less than 50% by weight of the total composition. In this case, the solvent may be selected from the group consisting of water-miscible solvents, in particular alcohols and ketones such as methanol, ethanol, isopropanol, 1-butanol, 2-butanol, or acetone. These can be used singly or in combination. The choice of solvent is mainly determined by the ease of handling and the ability to dissolve the components of the protective layer, but may also be influenced by other factors, such as flammability or toxicity.

In one embodiment, the co-solvent is absent, water being the only solvent. In a preferred aspect thereof, the solution consists of water and inorganic salts that are in a dissolved state to form solvated cations and anions. Herein, the salts preferably include monovalent cations, such as salts of the alkali metals, preferably sodium. In one embodiment, the cations in the solution are selected from sodium and magnesium, other cations being absent or being present in an amount of 10 mol % or less, such as 5 mol % or less, of all cations in the solution. Incidentally, throughout the invention, ions that are formed by dissociation of water (i.e. $H^+/H_3O^+$ and $OH^-$) are disregarded for the calculation of relative and total amounts of cations and anions in the solution, as their concentration determines the pH. Put differently, in the present invention the concentrations and amounts of anions and cations is expressed independently of the pH of the solution, and $H^+/H_3O^+$ and $OH^-$ are disregarded for the calculation of absolute and relative amounts of inorganic and organic cations and anions.

In one embodiment, the solution may or may not contain organic components and additives. These may in one embodiment be selected from the group consisting sugars, water-soluble polymers such as polyvinyl pyrrolidone (e.g. with number-average molecular weight of 15,000 or less or 10,000 or less), collagen, antioxidants or antifoulants, such as BHT, pharmaceutically active components, such as vitamins, antibacterial or disinfecting agents or antiobiotics.

The solution may or may not comprise organic salts. The term "organic salt" denotes a material which upon dissolution and dissociation in water forms cations and anions, and wherein either the cation or the anion is an organic compound containing carbon. Examples of such organic salt include sodium acetate, sodium acetyl acetonate, sodium formiate, etc., as well as pyridinium chloride, quaternary ammonium salts such as tetramethylammonium chloride, etc.

In one embodiment, the amount of organic components and additives is 10% by weight or less of the total weight of the composition, such as 5% by weight or less, e.g. 2% by weight or less. In one embodiment, such organic components and additives are absent.

In one embodiment, the aqueous solution does not contain an organic salt, nor any other organic compound or additive. In a preferred aspect of this embodiment, the salts are formed by sodium and magnesium salts only, and more preferably are formed from sodium and magnesium phosphates, hydrogen phosphates, dihydrogen phosphates, and chlorides.

In one embodiment, the solution comprises monovalent inorganic cations other than $H^+$ and $H_3O^+$ and monovalent, bivalent or trivalent inorganic anions. In one aspect of this embodiment, the monovalent inorganic cations are selected from the group consisting of $Na^+$, $K^+$, and $NH_4^+$, preferably $Na^+$ and $K^+$, more preferably $Na^+$. Herein, the amount of monovalent inorganic cations is preferably such that 50 mol % or more of all inorganic cations are selected from monovalent inorganic cations, preferably 60 mol % or more, such as 65 mol % or more or 70 mol % or more.

In one embodiment, the amount of monovalent inorganic cations is thus 50 mol % or more of all inorganic cations, preferably 60 mol % or more, such as 65 mol % or more or 70 mol % or more, and the monovalent inorganic cations are then selected from the group consisting of $Na^+$ and $K^+$. In one embodiment, the monovalent inorganic cation is $Na^+$, which is present in an amount of 50 mol % or more of all inorganic cations, preferably 60 mol % or more, such as 65 mol % or more or 70 mol % or more.

In one embodiment, $Na^+$ is present, $K^+$ is absent, and the remaining inorganic cations are preferably selected from the group consisting of bivalent inorganic cations, more preferably $Mg^{2+}$ and $Ca^{2+}$, further more preferably $Mg^{2+}$. In a preferred aspect, the inorganic cations are formed by only $Na^+$ and $Mg^{2+}$, i.e. the solution does not contain any cations other than $Na^+$ and $Mg^{2+}$. Herein, again, the amount of $Na^+$ is preferably 50 mol % or more of all inorganic cations, preferably 60 mol % or more, such as 65 mol % or more or 70 mol % or more.

The inorganic anions in the solution are not particularly limited, and any anion can be present as long as it forms a salt with the cations that is readily soluble in the body fluids. As a general guideline, a salt that dissolves in water in an amount of 50 g/l or more at 20° C., such as 100 g/l or more, 150 g/l or more, or even 200 g/l or more can be used in the solution of the present invention, with highly soluble salts being preferred. The combination of anions and cations should hence be chosen such that no salt with low solubility is formed, so that e.g. carbonates and hydrogen carbonates should be avoided, in particular if bivalent cations such as $Mg^{2+}$ and $Ca^{2+}$ are present, as this will lead to the formation of precipitation of only sparely soluble carbonate salts typically having a solubility of about 0.1 g/l at 20° C. Hence, in one embodiment the anions are selected from the group consisting of nitrate ($NO_3^-$), sulfate ($SO_4^{2-}$), halogens, in particular chloride ($Cl^-$), phosphate ($PO_4^{3-}$), hydrogen phosphate ($HPO_4^{2-}$) and dihydrogen phosphate ($H_2PO_4^-$).

In one embodiment, the solution does not contain any other salts but those selected from the chlorides, phosphates, hydrogen phosphates and dihydrogen phosphates of sodium and magnesium.

In one embodiment, the solution comprises sodium cations, and the sodium cations form 30-100 mol %, such as 50-99 mol % of the total of all alkaline and earth alkaline metal cations in the solution, and the solution comprises phosphate, hydrogen phosphate and/or dihydrogen phosphate anions, and the phosphate, hydrogen phosphate and/or dihydrogen phosphate anions form 30 mol % or more, such as 50 mol % or more, of the total of all inorganic anions. Herein, the alkali metal cations include all cations of metals in group 1 of the periodic table except hydrogen (i.e. Li, Na, K, Rb, Cs and Fr), and the earth alkali metal cations include all cations of group 2 of the periodic table (i.e. Be, Mg, Ca, Sr, Ba, and Ra).

In one embodiment, the solution comprises magnesium ions, and preferably the magnesium ions form 0.1-50 mol % of the total of all alkaline and earth alkaline metal cations in the solution. The remainder may then be formed by sodium and potassium cations, and preferably the remainder is formed by sodium cations.

In one embodiment, the solution does not contain calcium ions, and preferably also does not contain ammonium ions.

It has surprisingly been found that the pH of the solution has a great influence on the properties of the protective layer, and that a protective layer that has been formed from solution having a pH of 6.8 or less (at 25° C.) is superior in terms of removability and in providing, after dissolution of the protective layer, a surface that is highly hydrophilic (has a high surface energy). It is believed that both of these effects facilitate the incorporation of the implant or implantable component, as after dissolution of the protective layer, a highly hydrophilic and pure implant or implantable component surface can be provided. For instance, when the implant or implantable component is made from a metal or metal alloy, in particular titanium or a titanium alloy, the surface of the implant or implantable component after dissolution of the protective layer can exhibit a high density of hydroxyl groups, which is considered to facilitate the integration with the surrounding tissue.

While the effect is not yet fully understood, and without wishing to be bound by theory, it is believed that the charge of a surface (e.g. of a titanium or titanium alloy implant or implantable component) strongly depends on the pH of the solution it is immersed in. At low pH, the surface of the implant or implantable component surface (e.g. made from a metal or metal alloy, or also from a metal oxide, such as titanium oxide) is believed to be positively charged, and the surface charge gradually decreases in solution with increased pH. This is expressed by the isoelectric point, i.e. the pH at which there is a balance between positive and negative charges on the surface. For materials made from titanium, titanium alloys and titanium oxides, the isoelectric point is generally comprised between pH 4.0-6.8.

When the surface is negatively charged, cations in solution strongly interact with the surface, and are difficult to be rinsed off. Conversely, a positive charge may facilitate removal of cations, as these are less attracted to the surface.

By using a protective layer solution with a pH of 6.8 or lower, the interaction between the cations and the surface are weak, which may explain an easier removal of cations when rinsed in water or when contacting body fluids. Preferably, the pH of the solution is thus also lower than the isoelectric point of the surface on which the protective layer is to be formed.

It might further possibly be assumed that a low pH of 6.8 or lower might prevent or reduce the uptake of carbon dioxide and possibly other species from the atmosphere during preparation of the protective layer and/or during storage of the implant or implantable component having the protective layer. If carbon dioxide is absorbed, it forms carbonate and hydrogen carbonate ions in solution, which in turn form salts having relatively low solubility, in particular in combination with earth alkaline metal cations. Also, carbonates are a less hydrophilic material, and might thus facilitate the adsorption of organic contaminants to the protective layer surface. As the formation of carbonates is reduced or prevented with the solution for forming a protective layer of the present invention, the protective layer may dissolve more rapidly due to the absence or reduced amount of carbonates having low solubility, and contamination with organic substances might be prevented or reduced. This is a further reason why pH of the solution at 25° C. is thus 6.8 or less, such as 6.5 or less, 6.0 or less, 5.5 or less or 5.0 or less.

In one embodiment, the pH of the solution at 25° C. is thus below the isoelectric point of the surface of the implant or implantable component, which depending on the metal or alloy used, may be 6.8 or less such as 6.5 or less, 6.0 or less, 5.5 or less or 5.0 or less.

A highly acidic solution will also solve the problems of the present invention, but may possibly have a detrimental biological effect upon dissolution in the patient's body. Hence, the pH of the solution is preferably 0.0 or higher, 0.5 or higher or 1.0 or higher, such as 1.5 or higher or 2.0 or higher. The pH can thus e.g. be in the range from 2.8 to 3.4, from 3.6 to 4.9, or from 3.5 to 5.5.

Further, due its low pH, the protective layer preserves the amount of available functional groups (e.g. OH groups) on the surface of the implantable or implant component made from e.g. titanium during storage. This means that the protective layer is configured to reduce carbon deposition and preserve hydrophilicity and/or the density of free/unbound hydroxyl groups on the surface of the implantable or implant component during dry storage as compared to storage without said protective layer.

The protective layer of the present invention thus allows dry storage of an implant or implantable component. The present invention also encompasses the use of the protective layer obtainable by drying the solution as described herein for protecting an implantable or implant component during storage against contamination, wherein preferably the implantable or implant component is in a dry state during storage.

The salt concentration of the solution is not particularly limited, but can be adjusted by a skilled person in order to obtain the desired thickness of the protective layer. In one embodiment, the solution has a total concentration of inorganic salts of 1 to 200 mM, 2 to 50 mM or 5 to 20 mM, such as 7-10 mM, expressed as the total of all salts formed by the inorganic cations and the inorganic anions described above.

The salt concentration can be as high as 2, 4, 5, 7, 10, 20, 40, or 50 mM or higher, but can be as low as 180, 150 or 125 mM or lower. Within these ranges, a sufficiently thick salt layer can be formed by wetting or immersing the implant, followed by drying.

The protective layer formed from the solution described above protects the implantable or implant component during storage against contamination. This means that the amount of contaminants is reduced as compared to an implantable or implant component not having the protective layer.

The protective layer also preserves the hydrophilicity of the implantable or implant component during storage. Accordingly, a highly hydrophilic surface of the implantable or implant component can be maintained and revealed again after the protective layer is removed/dissolved. To achieve this, the surface must either by hydrophilic (i.e. must have an increased free surface energy) prior to application of the solution, or is must be rendered hydrophilic at the same time when the solution is applied. In one embodiment, hence the implantable or implant component exhibits a water contact angle of 0-30 both prior to application of the solution in step a) and after removal of the protective layer, assessed by rinsing the implant or component with water at 25° C. for 2 minutes, followed by drying.

It follows that in one embodiment of the method for forming a protective layer of the present invention, the method further comprises a step for increasing the free surface energy of the implantable or implant component prior to or simultaneous with the application of the solution in step a). This can be effected by a number of ways known to a skilled person, such as acid etching with an inorganic acid, such as HF, HCl, $H_2SO_4$ or mixtures thereof, UV irradiation, oxidation with oxygen peroxide, plasma treatment, etc. Also, the method described in EP 0 388 576 may be employed.

The protective layer formed from the solution as described above can be easily removed when implanted. This can be assessed by testing the removal of the elements of the protective layer in a rinsing test. In one embodiment, after rinsing the implant or component with water at 25° C. for 2 minutes (e.g. by putting it under a flow of gently flowing water), 30 atom % or less, such as 20 atom % or less, preferably less than 10 atom % of the protective layer remain on the surface. This can be assessed by any suitable surface analysis technique, such as XPS or Auger.

After the solution is applied in step a), it is dried in step b). The application can be performed by any suitable technique, such as coating, spraying or dipping/immersing the implantable or implant component into the solution.

The following process parameters may be adhered to:

Process parameters during application:

Temperature: generally 0-100° C., preferably 20-90° C.

Pressure: usually atmospheric pressure;

Time: sufficient to ensure complete wetting, such as 5 seconds or longer, but typically 5 minutes or less;

Process parameters during drying:

Temperature: sufficient to enable drying, preferably 30-95° C., more preferably 50-90° C.

Time: sufficient to achieve dry state, preferably 15-120 minutes, more preferably 30-100 minutes Pressure: atmospheric pressure (1 atm) or less, such as 50-770 mm Hg.

Generally, a drying at moderate temperatures for longer duration and under relatively high pressure may be preferred in order to avoid the formation of a highly porous layer that may not completely cover the implant surface.

The implantable or implant component is not particularly limited, but is preferably an implantable or implant component that is made from metal, a metal alloy, a plastic material and a ceramic material. Preferably, the implantable or implant component is made from a metal or metal alloy, with titanium and a titanium alloy being particularly preferable.

The implantable or implant component is also not limited with respect to its form and shape, and any implantable or implant component may be subject to the method and use of the present invention. This includes e.g. hip implants, knee implants, implants designed as replacement of parts of the arms or legs, and dental implant and dental implant components, such abutments, crowns and bridges. The implantable or implant component is preferably a dental implantable or implant component, more preferably a dental implant or a dental implant abutment. In one embodiment, the implantable or implant component may be the implant, the implant system or the component also disclosed in the present disclosure.

The present invention not only includes the method for forming a protective layer and the use of the layer for protecting an implant or implantable component during storage as described above, but also envisages that the solution per se is an inventive contribution to the art. The solution that has been described above with respect to the method and the use is thus considered to be claimable aspect of the present invention, and this includes all embodiments and preferred aspects of the solution that has been described above for the method and the use.

The thickness of the protective layer is not particularly limited, and a low thickness may be sufficient to obtain the desired protection. The thickness is determined by the concentration of the protective layer components in the solution and the application amount of the solution. The thickness may be between 0.1-20 µm, such as 0.2-5 µm. or 0.3-3.1 µm.

The present invention also encompasses a package containing an implant or implantable component having the protective layer as described above. The package may be filled with the dry implantable or implant component having the protective layer in an atmosphere that is selected from air, nitrogen or other inert gases. As the implant is protected by the protective layer, air may be used, and the package does not need to be airtight. Optionally, a sterilization with e.g. ethylene oxide gas may be applied, which may be effected prior to packaging or even after packaging has taken place, due to the ethylene oxide gas permeating into the packaging.

Example 1—Effect of the Salt Composition

The effects of the salt composition were assessed by preparing aqueous solutions containing only water as the solvent with the following compositions:

| | |
|---|---|
| 38.5 mM $Na_2HPO_4$+7.15 mM $NaH_2PO_4$+2.5 mM $MgCl_2$ | Solution 1 |

| | |
|---|---|
| 38.5 mM $K_2HPO_4$+7.15 mM $KH_2PO_4$+2.5 mM $MgCl_2$ | Solution 2 |

Titanium implants were wetted with Solution 1 or 2, respectively, and dried to obtain a salt layer on the implant.

In order to assess whether the salt layer could be removed by a simple washing process, each implant was rinsed 3 times in 10 ml water. Thereafter, the remaining salt layer elements were assessed by Auger spectroscopy. It was found that for the salt layer obtained from Solution 1, 15% of the elements remained on the surface of the implant, while for the salt layer obtained from Solution 2, 26% of the elements remained on the surface. This shows that the sodium-based solution can be more easily removed than a potassium-based solution.

Example 2—Influence of pH and Surface Energy

In order to assess the influence of pH, Example 1 was performed with two modifications of Solution 1 having the same salt concentration, but a pH of 7.1 or 4.0, respectively. It was found that, again after rinsing 3 times with 10 ml water, the salt layer obtained from the solution having a pH of 7.1 led to 15 atom % of remaining elements on the surface, while for the solution having a pH of 4.0, only 3 atom % of the elements stayed on the surface.

This shows that adjusting the pH of the solution to acidic values allows obtaining a layer that can more easily and completely be removed.

In a further test, it was evaluated whether the surface energy of the implant substrate influences the removability of the salt layer. Two tests were performed with Solution 1, one on an implant having a high surface energy (water contact angle=0°) and one on an implant having a low surface energy (water contact angle=47°). It was found that after rinsing the implant 3 times with 10 ml water, for the implant with high surface area 15 atom % of the elements of the salt layer remained on the surface, while for the implant with low surface energy only 2% of the elements remained on the surface. This shows that the removal is facilitated by a lower surface energy of the underlying implant surface.

Example 3—Protective Effect Against Contamination

To test the efficacy of the protective layer in protecting the surface from adsorbing atmospheric elements molecules, the carbon content was measured on abutment surfaces stored in an environmental chamber (set at 25° C. and 50% humidity) with or without protective layer.

Abutment surfaces were UV-ozone treated for 15 min, if applicable an protective layer formed from the above Solution 1 was applied and dried, and the resulting abutment was handled in a protective environment of a nitrogen filled glove-box (these samples are referred as time 0). The samples with or without protective layer were exposed to air for 2 minutes, 1 hour or 3 days. Other samples, not initially UV cleaned, were used as the final time point (t inf.). For each time point, samples were rinsed in ultra-pure water and blow dried with a nitrogen stream. The carbon content at the surface was determined as atomic percentage by XPS or Auger spectroscopy (see also FIG. 4B).

During storage, hydrocarbons and other atmospheric elements deposit on the surface. Carbon accumulation was confirmed by assessing the carbon content on UV-ozone cleaned abutment 7.2 at %. When exposed to atmospheric conditions, the carbon content rapidly increases to 13.4 at % after 2 min, 14.3 at % after 1 hour and 20.4 at % after 72 h. Interestingly, when the abutment featured the protective salt layer obtained from Solution 1, the carbon content was consistently lower, reaching 12.4 at % after 72 h. The carbon content on abutments that were not UV cleaned and stored in standard packaging (Inf) remained also significantly lower when the salt layer was applied compared to abutments without salt layer (14.6 at % versus 34.9 at %, respectively). See also FIG. 4B.

Beside the carbon content, the ratio of other elements composing the surface were not significantly different after rinsing off the device, showing the full dissolution of the protective layer. This data suggests that the layer indeed fully dissolved, revealing a pristine surface as indicated by the low carbon levels after rinsing.

It is further known that the surface energy, correlated to the hydrophilicity, decreases with atmospheric contaminants depositing on the surface. The assessment of the hydrophilicity of stored samples confirmed the preservation of high surface energy and hydroxyl groups as indicated by a contact angle of 0°, compared to samples stored without protective salt layer (contact angle: 46.3±5.6°), confirming a lower carbon content and higher surface energy of samples stored with the protective layer obtained from the solution of the present invention (see also FIG. 4C).

Lastly, no difference in cell proliferation was observed in response to the protective layer, whether for keratinocytes seeded on abutments nor for MSC seeded on implants (see FIGS. 4E and 4F, respectively), confirming the cell-friendliness of the protective layer.

The invention claimed is:

1. Dental implant configured to be inserted into a hole in jaw bone and to be at least partially situated in bone tissue when implanted, comprising:
   a coronal implant region having a surface, wherein
      the surface is at least partly covered by an oxide layer with an average thickness in the range from 60 nm to 170 nm such that the coronal implant region exhibits a yellow color when viewed by the human eye, wherein the oxide layer on the surface of the coronal implant region comprises predominantly or consists of amorphous titanium oxide and
      the surface has an average arithmetical mean height surface roughness Sa in the range from 0.1 μm to 1.0 μm.

2. Dental implant according to claim 1, wherein the surface of the coronal implant region is smooth, non-porous, nanostructured and/or exhibits an as-machined structure.

3. Dental implant according to claim 1, wherein the surface of the coronal implant region has an average arithmetical mean height Sa in the range from 0.2 μm to 0.8 μm.

4. Dental implant according to claim 1, further comprising:
   a transition implant region;
   an apical implant region;
   a longitudinal axis extending from the coronal implant region to the apical implant region; wherein
   the sequence of regions starting from a coronal end of the dental implant to an apical end of the dental implant along the longitudinal axis is: the coronal implant region—the transition implant region—the apical implant region, and
   at least one of the following applies with respect to the surface properties of said regions:
      average arithmetical mean height Sa of the apical implant region>Sa of the transition implant region>Sa of the coronal implant region,
      average developed interfacial area ratio Sdr of the apical implant region>Sdr of the transition implant region>Sdr of the coronal implant region,
      average thickness of an oxide layer dox on an implant surface of the apical implant region>$d_{OX}$ of that of the transition implant region>$d_{OX}$ of that of the coronal implant region, and average phosphorous content $C_P$ of the oxide layer of the apical implant region>$C_P$ of that of the transition implant region>$C_P$ of that of the coronal implant region.

5. Dental implant according to claim 1, wherein surface properties of an apical implant region, a transition implant region and the coronal implant region change in a stepwise manner or a continuous manner, or combinations thereof between the different regions along the longitudinal axis of the dental implant.

6. Dental implant according to claim 1, wherein, in an apical implant region, a transition implant region and/or the coronal implant region, the oxide layer further comprises calcium, magnesium and/or fluoride; and/or the surface of the apical implant region and the transition implant region are microporous surfaces and/or comprise at least one of a bone-growth-initiating and a bone-growth-stimulating substance.

7. Dental implant according to claim 1, wherein the surface of an apical implant region exhibits at least one of:
average Sa: 1.50 μm±0.4 μm,
average Sdr: 187%±50%,
mean pore diameter: 1.5 μm±0.5 μm,
average oxide layer thickness dox: 9000 nm±3000 nm, and
average phosphorus content $C_P$: in a range from 4% to 12%, and/or
the surface of a transition implant region exhibits at least one of:
average Sa: 0.8 μm±0.5 μm,
average Sdr: 148%±40%,
mean pore diameter: 1.0 μm±0.5 μm
average oxide layer thickness dox: 7000 nm±3000 nm, and
average phosphorus content $C_P$: in a range from 3% to 11%, and/or
the surface of the coronal implant region exhibits at least one of:
average Sa: 0.5 μm±0.3 μm,
average Sdr: 16.6%±15%,
mean Nanostructure size: 80 nm±50 nm,
average oxide layer thickness dox: 120 nm±40 nm, and
average phosphorus content $C_P$: in a range from 2% to 6%.

8. Dental implant according to claim 1, wherein surface properties of an apical implant region, a transition implant region and the coronal implant region are at least partially obtainable by performing an anodic oxidation process.

9. Dental implant according to claim 1, wherein the surfaces of a transition implant region and/or an apical implant region are obtainable by performing a spark anodization process.

10. Dental implant according to claim 1, wherein a base material of the dental implant comprises titanium or a titanium alloy.

11. Dental implant according to claim 10, wherein an oxide layer on the surface of an apical implant region and a transition implant region comprises crystalline titanium oxide in the anatase phase, and the remainder comprises rutile and/or amorphous titanium oxide.

12. Dental implant according to claim 11, wherein the oxide layer on the surface of the apical implant region and the transition implant region comprises crystalline titanium oxide in the anatase phase in the range of 70-100%.

13. Dental implant according to claim 1, wherein,
a) the coronal implant region extends from a coronal end of the dental implant up to 2 mm±0.5 mm along the longitudinal axis towards an apical end of the dental implant,
a transition implant region extends from said 2 mm±0.5 mm up to 4 mm±0.5 mm further along the longitudinal axis towards the apical end of the dental implant, and
an apical implant region extends from said 4 mm±0.5 mm up to the apical end of the dental implant
or
b) the coronal implant region has a length measured from a coronal end of the dental implant along the longitudinal axis towards an apical end of the dental implant from 0.5 mm to 6.0 mm.

14. Dental implant according to claim 1, wherein the oxide layer on the surface of the coronal implant region is virtually non-crystalline and/or anatase-free.

15. Dental implant according to claim 1, wherein the oxide layer on the surface of the coronal implant region consists of amorphous titanium oxide.

16. Dental implant according to claim 1, wherein the oxide layer on the surface of the coronal implant region is virtually non-crystalline.

\* \* \* \* \*